United States Patent
Wu

(10) Patent No.: US 10,330,629 B2
(45) Date of Patent: *Jun. 25, 2019

(54) SYSTEM ERROR COMPENSATION OF ANALYTE CONCENTRATION DETERMINATIONS

(71) Applicant: Bayer HealthCare LLC, Whippany, NJ (US)

(72) Inventor: Huan-Ping Wu, Granger, IN (US)

(73) Assignee: Ascensia Diabetes Care Holdings AG, Basel (CH)

( * ) Notice: Subject to any disclaimer, the term of this patent is extended or adjusted under 35 U.S.C. 154(b) by 684 days.

This patent is subject to a terminal disclaimer.

(21) Appl. No.: 14/774,684

(22) PCT Filed: Mar. 11, 2014

(86) PCT No.: PCT/US2014/023069
§ 371 (c)(1),
(2) Date: Sep. 10, 2015

(87) PCT Pub. No.: WO2014/159333
PCT Pub. Date: Oct. 2, 2014

(65) Prior Publication Data
US 2016/0025673 A1    Jan. 28, 2016

Related U.S. Application Data

(60) Provisional application No. 61/781,950, filed on Mar. 14, 2013.

(51) Int. Cl.
*G01N 27/327* (2006.01)
*G01N 33/72* (2006.01)

(52) U.S. Cl.
CPC ....... *G01N 27/3274* (2013.01); *G01N 33/723* (2013.01)

(58) Field of Classification Search
None
See application file for complete search history.

(56) References Cited

U.S. PATENT DOCUMENTS

| | | | |
|---|---|---|---|
| 5,620,579 | A | 4/1997 | Genshaw |
| 5,653,863 | A | 8/1997 | Genshaw |
| 6,120,676 | A | 9/2000 | Heller |
| 6,153,069 | A | 11/2000 | Pottgen |
| 6,413,411 | B1 | 7/2002 | Pottgen |
| 2009/0177406 | A1 | 7/2009 | Wu |
| 2010/0170807 | A1 | 7/2010 | Diebold |
| 2011/0231105 | A1 | 9/2011 | Wu |
| 2013/0071869 | A1 | 3/2013 | Wu |

FOREIGN PATENT DOCUMENTS

| | | |
|---|---|---|
| CN | 101999073 | 3/2011 |
| WO | WO 2007/013915 | 2/2007 |
| WO | WO 2007/040913 | 4/2007 |
| WO | WO 2010/077660 | 7/2010 |

OTHER PUBLICATIONS

Search Report for International Application No. PCT/US2014/023069 dated Jul. 30, 2014 (3 pages).
Written Opinion for International Application No. PCT/US2014/023069 dated Jul. 30, 2014 (8 pages).

*Primary Examiner* — G Steven Vanni
(74) *Attorney, Agent, or Firm* — Nixon Peabody LLP

(57) ABSTRACT

During analyte analysis, errors may be introduced into an analysis by both the biosensor system used to perform the analysis and by errors in the output signal measured by the measurement device of the biosensor. For a reference sample, system error may be determined through the determination of relative error. However, during an analysis of a test sample with the measurement device of the biosensor system, true relative error cannot be known. A pseudo-reference concentration determined during the analysis may be used as a substitute for true relative error. The present invention introduces the determination of a pseudo-reference concentration determined during the analysis as a substitute for the true relative error and uses an anchor parameter to compensate for the system error in the analysis-determined pseudo-reference concentration.

15 Claims, 17 Drawing Sheets

SYSTEM ERROR COMPENSATION OF ANALYTE CONCENTRATION DETERMINATIONS

REFERENCE TO RELATED APPLICATIONS

This application claims the benefit of U.S. Provisional Patent Application No. 61/781,950 entitled "Compensation of Analyte Concentration Determinations Through Linkage of System and Signal Errors" filed Mar. 14, 2013, which is incorporated by reference in its entirety.

BACKGROUND

Biosensor systems provide an analysis of a biological fluid sample, such as blood, serum, plasma, urine, saliva, interstitial, or intracellular fluid. Typically, the systems include a measurement device that analyzes a sample residing in a test sensor. The sample usually is in liquid form and in addition to being a biological fluid, may be the derivative of a biological fluid, such as an extract, a dilution, a filtrate, or a reconstituted precipitate. The analysis performed by the biosensor system determines the presence and/or concentration of one or more analytes, such as alcohol, glucose, uric acid, lactate, cholesterol, bilirubin, free fatty acids, triglycerides, proteins, ketones, phenylalanine or enzymes, in the biological fluid. For example, a person with diabetes may use a biosensor system to determine the A1c or glucose level in blood for adjustments to diet and/or medication.

In blood samples including hemoglobin (Hb), the presence and/or concentration of total hemoglobin (THb) and glycated hemoglobin (HbA1c) may be determined. HbA1c (%-A1c) is a reflection of the state of glucose control in diabetic patients, providing insight into the average glucose control over the three months preceding the test. For diabetic individuals, an accurate measurement of %-A1c assists in determining how well the patient is controlling blood glucose levels with diet and/or medication over a longer term than provided by an instantaneous measure of blood glucose level. As an instantaneous blood glucose measurement does not indicate blood glucose control other than when the measurement is made.

Biosensor systems may be designed to analyze one or more analytes and may use different volumes of biological fluids. Some systems may analyze a single drop of blood, such as from 0.25-15 microliters (μL) in volume. Biosensor systems may be implemented using bench-top, portable, and like measurement devices. Portable measurement devices may be hand-held and allow for the identification and/or quantification of one or more analytes in a sample. Examples of portable measurement systems include the Contour® meters of Bayer HealthCare in Tarrytown, N.Y., while examples of bench-top measurement systems include the Electrochemical Workstation available from CH Instruments in Austin, Tex.

Biosensor systems may use optical and/or electrochemical methods to analyze the biological fluid. In some optical systems, the analyte concentration is determined by measuring light that has interacted with or been absorbed by a light-identifiable species, such as the analyte or a reaction or product formed from a chemical indicator reacting with the analyte. In other optical systems, a chemical indicator fluoresces or emits light in response to the analyte when illuminated by an excitation beam. The light may be converted into an electrical output signal, such as current or potential, which may be similarly processed to the output signal from an electrochemical system. In either optical system, the system measures and correlates the light with the analyte concentration of the sample.

In light-absorption optical systems, the chemical indicator produces a reaction product that absorbs light. A chemical indicator such as tetrazolium along with an enzyme such as diaphorase may be used. Tetrazolium usually forms formazan (a chromagen) in response to the redox reaction of the analyte. An incident input beam from a light source is directed toward the sample. The light source may be a laser, a light emitting diode, or the like. The incident beam may have a wavelength selected for absorption by the reaction product. As the incident beam passes through the sample, the reaction product absorbs a portion of the incident beam, thus attenuating or reducing the intensity of the incident beam. The incident beam may be reflected back from or transmitted through the sample to a detector. The detector collects and measures the attenuated incident beam (output signal). The amount of light attenuated by the reaction product is an indication of the analyte concentration in the sample.

In light-generated optical systems, the chemical indicator fluoresces or emits light in response to the analyte redox reaction. A detector collects and measures the generated light (output signal). The amount of light produced by the chemical indicator is an indication of the analyte concentration in the sample and is represented as a current or potential from the detector.

An example of an optical system using reflectance is a laminar flow %-A1c system that determines the concentration of A1c hemoglobin in blood. These systems use immunoassay chemistry where the blood is introduced to the test sensor of the biosensor system where it reacts with reagents and then flows along a reagent membrane. When contacted by the blood, A1c antibody coated color beads release and move along with the blood to a detection Zone 1. Because of the competition between the A1c in the blood sample and an A1c peptide present in detection Zone 1 for the color beads, color beads not attached to the A1c antibody are captured at Zone 1 and are thus detected as the A1c signal from the change in reflectance. The total hemoglobin (THb) in the blood sample also is reacting with other blood treatment reagents and moves downstream into detection Zone 2, where it is measured at a different wavelength. For determining the concentration of A1c in the blood sample, the reflectance signal is proportional to the A1c analyte concentration (%-A1c), but is affected by the THb content of the blood. For the THb measurement, however, the reflectance in Zone 2 is inversely proportional to the THb (mg/mL) of the blood sample, but is not appreciably affected by the A1c content of the blood.

In electrochemical systems, the analyte concentration of the sample is determined from an electrical signal generated by an oxidation/reduction or redox reaction of the analyte or a measurable species responsive to the analyte concentration when an input signal is applied to the sample. The input signal may be a potential or current and may be constant, variable, or a combination thereof such as when an AC signal is applied with a DC signal offset. The input signal may be applied as a single pulse or in multiple pulses, sequences, or cycles. An enzyme or similar species may be added to the sample to enhance the electron transfer from the analyte during the redox reaction. The enzyme or similar species may react with a single analyte, thus providing specificity to a portion of the generated output signal. A redox mediator may be used as the measurable species to maintain the oxidation state of the enzyme and/or assist with electron transfer from the analyte to an electrode. Thus, during the redox reaction, an enzyme or similar species may transfer electrons between the analyte and the redox mediator, while the redox mediator transfers electrons between itself and an electrode of the test sensor.

Electrochemical biosensor systems usually include a measurement device having electrical contacts that connect with the electrical conductors of the test sensor. The conductors may be made from conductive materials, such as solid metals, metal pastes, conductive carbon, conductive carbon pastes, conductive polymers, and the like. The electrical conductors connect to working and counter electrodes, and may connect to reference and/or other electrodes that extend into a sample reservoir depending on the design of the test sensor. One or more electrical conductors also may extend into the sample reservoir to provide functionality not provided by the electrodes.

In many biosensor systems, the test sensor may be adapted for use outside, inside, or partially inside a living organism. When used outside a living organism, a sample of the biological fluid may be introduced into a sample reservoir in the test sensor. The test sensor may be placed in the measurement device before, after, or during the introduction of the sample for analysis. When inside or partially inside a living organism, the test sensor may be continually immersed in the sample or the sample may be intermittently introduced to the test sensor. The test sensor may include a reservoir that partially isolates a volume of the sample or be open to the sample. When open, the test sensor may take the form of a fiber or other structure placed in contact with the biological fluid. Similarly, the sample may continuously flow through the test sensor, such as for continuous monitoring, or be interrupted, such as for intermittent monitoring, for analysis.

The measurement device of an electrochemical biosensor system applies an input signal through the electrical contacts to the electrical conductors of the test sensor. The electrical conductors convey the input signal through the electrodes into the sample present in the sample reservoir. The redox reaction of the analyte generates an electrical output signal in response to the input signal. The electrical output signal from the test sensor may be a current (as generated by amperometry or voltammetry), a potential (as generated by potentiometry/galvanometry), or an accumulated charge (as generated by coulometry). The measurement device may have the processing capability to measure and correlate the output signal with the presence and/or concentration of one or more analytes in the sample.

In coulometry, a potential is applied to the sample to exhaustively oxidize or reduce the analyte. A biosensor system using coulometry is described in U.S. Pat. No. 6,120,676. In amperometry, an electric signal of constant potential (voltage) is applied to the electrical conductors of the test sensor while the measured output signal is a current. Biosensor systems using amperometry are described in U.S. Pat. Nos. 5,620,579; 5,653,863; 6,153,069; and 6,413,411. In voltammetry, an electric signal of varying potential is applied to a sample of biological fluid, while the measured output is current. In gated amperometry and gated voltammetry, pulsed inputs are used as described in WO 2007/013915 and WO 2007/040913, respectively.

Primary output signals are responsive to the analyte concentration of the sample and are obtained from an analytic input signal. Output signals that are substantially independent of signals responsive to the analyte concentration of the sample include signals responsive to temperature and signals substantially responsive to interferents, such as the hematocrit or acetaminophen content of a blood sample when the analyte is glucose, for example. Output signals substantially not responsive to analyte concentration may be referred to as secondary output signals, as they are not primary output signals responsive to the alteration of light by the analyte or analyte responsive indicator, the electrochemical redox reaction of the analyte, or the electrochemical redox reaction of the analyte responsive redox mediator. Secondary output signals are responsive to the physical or environmental characteristics of the biological sample. Secondary output signals may arise from the sample or from other sources, such as a thermocouple that provides an estimate of an environmental characteristic of the sample. Thus, secondary output signals may be determined from the analytic input signal or from another input signal.

When arising from the sample, secondary output signals may be determined from the electrodes used to determine the analyte concentration of the sample, or from additional electrodes. Additional electrodes may include the same reagent composition as the electrodes used to determine the analyte concentration of the sample, a different reagent composition, or no reagent composition. For example, a reagent composition may be used that reacts with an interferent or an electrode lacking reagent composition may be used to study one or more physical characteristics of the sample, such as whole blood hematocrit.

The measurement performance of a biosensor system is defined in terms of accuracy and precision. Accuracy reflects the combined effects of systematic and random error components. Systematic error, or trueness, is the difference between the average value determined from the biosensor system and one or more accepted reference values for the analyte concentration of the biological fluid. Trueness may be expressed in terms of mean bias, with larger mean bias values representing lower trueness and thereby contributing to less accuracy. Precision is the closeness of agreement among multiple analyte readings in relation to a mean. One or more error in the analysis contributes to the bias and/or imprecision of the analyte concentration determined by the biosensor system. A reduction in the analysis error of a biosensor system therefore leads to an increase in accuracy and/or precision and thus an improvement in measurement performance.

Bias may be expressed in terms of "absolute bias" or "percent bias". Absolute bias is the difference between the determined concentration and the reference concentration, and may be expressed in the units of the measurement, such as mg/dL, while percent bias may be expressed as a percentage of the absolute bias value over the reference concentration, or expressed as a percentage of the absolute bias over either the cut-off concentration value or the reference concentration of the sample. For example, if the cut-off concentration value is 100 mg/dL, then for glucose concentrations less than 100 mg/dL, percent bias is defined as (the absolute bias over 100 mg/dL)*100; for glucose concentrations of 100 mg/dL and higher, percent bias is defined as the absolute bias over the accepted reference value of analyte concentration*100.

Accepted reference values for the analyte glucose in blood samples are preferably obtained with a reference instrument, such as the YSI 2300 STAT PLUS™ available from YSI Inc., Yellow Springs, Ohio. Other reference instruments and ways to determine percent bias may be used for other analytes. For the %-A1c measurements, the error may be expressed as either absolute bias or percent bias against the %-A1c reference value for the therapeutic range of 4-12%. Accepted reference values for the %-A1c in blood samples may be obtained with a reference instrument, such as the Tosoh G7 instrument available from Tosoh Corp, Japan.

Biosensor systems may provide an output signal during the analysis of the biological fluid including error from multiple error sources. These error sources contribute to the total error, which may be reflected in an abnormal output signal, such as when one or more portions or the entire output signal is non-responsive or improperly responsive to the analyte concentration of the sample.

The total error in the output signal may originate from one or more error contributors, such as the physical characteristics of the sample, the environmental aspects of the sample, the operating conditions of the system, the manufacturing variation between test sensor lots, and the like. Physical characteristics of the sample include hematocrit (red blood cell) concentration, interfering substances, such as lipids and proteins, and the like. Interfering substances for glucose analyses also may include ascorbic acid, uric acid, acetaminophen, and the like. Environmental aspects of the sample include temperature, oxygen content of the air, and the like. Operating conditions of the system include underfill conditions when the sample size is not large enough, slow-filling of the test sensor by the sample, intermittent electrical contact between the sample and one or more electrodes of the test sensor, degradation of the reagents that interact with the analyte after the test sensor was manufactured, and the like. Manufacturing variations between test sensor lots include changes in the amount and/or activity of the reagents, changes in the electrode area and/or spacing, changes in the electrical conductivity of the conductors and electrodes, and the like. A test sensor lot is preferably made in a single manufacturing run where lot-to-lot manufacturing variation is substantially reduced or eliminated. There may be other contributors or a combination of error contributors that cause error in the analysis.

Percent bias, mean percent bias, percent bias standard deviation (SD), percent coefficient of variance (%-CV), and hematocrit sensitivity are independent ways to express the measurement performance of a biosensor system. Additional ways may be used to express the measurement performance of a biosensor system.

Percent bias is a representation of the accuracy of the biosensor system in relation to a reference analyte concentration, while the percent bias standard deviation reflects the accuracy of multiple analyses, with regard to error arising from the physical characteristics of the sample, the environmental aspects of the sample, the operating conditions of the system, and the manufacturing variations between test sensors. Thus, a decrease in percent bias standard deviation represents an increase in the measurement performance of the biosensor system across multiple analyses. The percent coefficient of variance may be expressed as 100%*(SD of a set of samples)/(the average of multiple readings taken from the same set of samples) and reflects precision of multiple analyses. Thus, a decrease in percent bias standard deviation represents an increase in the measurement performance of the biosensor system across multiple analyses.

The mean may be determined for the percent biases determined from multiple analyses using test sensors from a single lot to provide a "mean percent bias" for the multiple analyses. The mean percent bias may be determined for a single lot of test sensors by using a subset of the lot, such as 80-140 test sensors, to analyze multiple blood samples.

Increasing the measurement performance of the biosensor system by reducing error from these or other sources means that more of the analyte concentrations determined by the biosensor system may be used for accurate therapy by the patient when blood glucose is being monitored, for example. Additionally, the need to discard test sensors and repeat the analysis by the patient also may be reduced.

Biosensor systems may have a single source of uncompensated output signals responsive to a redox or light-based reaction of the analyte, such as the counter and working electrodes of an electrochemical system. Biosensor systems also may have more than one source of uncompensated output responsive or non-responsive to the analyte concentration of the sample. For example, in an A1c biosensor, there may be one or more output signals responsive to the analyte concentration of the sample, but there also may be one or more output signals responsive to total hemoglobin (THb) that is not responsive to the analyte concentration of the sample, but which affect the analyte responsive signal/s.

Accordingly, there is an ongoing need for improved biosensor systems, especially those that may provide increasingly accurate determination of sample analyte concentrations through compensation. Many biosensor systems include one or more methods to compensate error associated with an analysis, thus attempting to improve the measurement performance of the biosensor system. Compensation methods may increase the measurement performance of a biosensor system by providing the biosensor system with the ability to compensate for inaccurate analyses, thus increasing the accuracy and/or precision of the concentration values obtained from the system.

However, these methods have had difficulty compensating the errors in the analysis reflected as a whole by the biosensor system error and error originating from the output signal error. Issues also may arise if the error parameters chosen to describe or compensate for the desired error contributors do not well-describe the error arising during the analysis. A collection of such relatively weak error parameters may be less stable than expected even though the overall correlation of is relatively strong. The present invention avoids or ameliorates at least some of the disadvantages of analyte concentration determination systems lacking compensation for both system and output signal errors.

SUMMARY

In one aspect, the invention provides a method for determining an analyte concentration in a sample that includes generating at least one output signal from a sample; measuring at least one analyte responsive output signal from the sample; determining a pseudo-reference concentration value from the at least one analyte responsive output signal, where a pseudo-reference concentration value is a substitute for true relative error; determining at least one anchor parameter in response to the pseudo-reference concentration value, where the at least one anchor parameter compensates for system error; incorporating the at least one anchor parameter into a compensation relationship; and determining a final compensated analyte concentration of the sample in response to the compensation relationship.

In another aspect of the invention, there is a method for determining signal-based anchor parameters that includes generating at least one output signal from the sample; determining at least one normalized output signal from the at least one output signal; determining a pseudo-reference concentration value for the sample; determining at least one corresponding normalized output signal in response to at least one reference sample analyte concentration and a normalized reference correlation; determining system error for the at least one output signal; and determining at least one signal-based anchor parameter for at least one primary analyte responsive output signal, where the at least one signal-based anchor parameter compensates for system error.

In another aspect of the invention, there is a method for determining concentration-based anchor parameters that includes generating at least one output signal from the sample; determining a pseudo-reference concentration value for the sample from the at least one output signal; determining system error for the at least one output signal; and determining at least one concentration-based anchor parameter for each of the at least two initial analyte concentrations, where the at least one concentration-based anchor parameter compensates for system error.

In another aspect of the invention, there is a method to determine a compensation relationship for system error in an analyte analysis that includes selecting at least two segmented signal processing (SSP) parameters and at least one anchor parameter as potential terms in a compensation relationship, where the at least two SSP segmented signal processing parameters are responsive to at least one time-based signal profile, and where the at least one anchor parameter compensates for system error; determining a first exclusion value for each potential term in response to a mathematical technique; applying at least one exclusion test to the first exclusion values to identify at least one potential term to exclude from the compensation relationship; determining at least one second exclusion value for the remaining potential terms; if the at least one second exclusion value does not identify remaining potential terms to exclude from the compensation relationship, including the remaining potential terms in the compensation relationship; if the at least one second exclusion value identifies remaining terms to exclude from the compensation relationship under the at least one exclusion test, determining at least one third exclusion value for each remaining potential term; repeat applying the at least one exclusion test to subsequent exclusion values until the at least one exclusion test fails to identify at least one potential term to exclude from the compensation relationship; and when the repeated at least one exclusion test does not identify remaining potential terms to exclude from the compensation relationship, including the remaining potential terms in the compensation relationship.

In another aspect of the invention, there is an analyte measurement device that includes electrical circuitry connected to a sensor interface, where the electrical circuitry includes a processor connected to a signal generator and a storage medium; where the processor is capable of measuring at least one analyte responsive output signal; where the processor is capable of determining a pseudo-reference concentration value from the at least one analyte responsive output signal, where a pseudo-reference concentration value is a substitute for true relative error; where the processor is capable of determining at least one anchor parameter in response to the pseudo-reference concentration value, where the at least one anchor parameter compensates for system error; where the processor is capable of incorporating the at least one anchor parameter into a compensation relationship; and where the processor is capable of determining a final compensated analyte concentration of the sample in response to the compensation relationship.

In another aspect of the invention, there is a biosensor system for determining an analyte concentration in a sample that includes a test sensor having a sample interface adjacent to a reservoir formed by a base, where the test sensor is capable of generating at least one output signal from a sample; and a measurement device having a processor connected to a sensor interface, the sensor interface having electrical communication with the sample interface, and the processor having electrical communication with a storage medium; where the processor is capable of measuring at least one analyte responsive output signal; where the processor is capable of determining a pseudo-reference concentration value from the at least one analyte responsive output signal, where a pseudo-reference concentration value is a substitute for true relative error; where the processor is capable of determining at least one anchor parameter in response to the pseudo-reference concentration value, where the at least one anchor parameter compensates for system error; where the processor is capable of incorporating the at least one anchor parameter into a compensation relationship; and where the processor is capable of determining a final compensated analyte concentration of the sample in response to the compensation relationship.

BRIEF DESCRIPTION OF THE DRAWINGS

The invention can be better understood with reference to the following drawings and description. The components in the figures are not necessarily to scale, emphasis instead being placed upon illustrating the principles of the invention.

FIG. 28 depicts a schematic representation of a biosensor system that determines an analyte concentration in a sample of a biological fluid.

DETAILED DESCRIPTION

Figure 1:
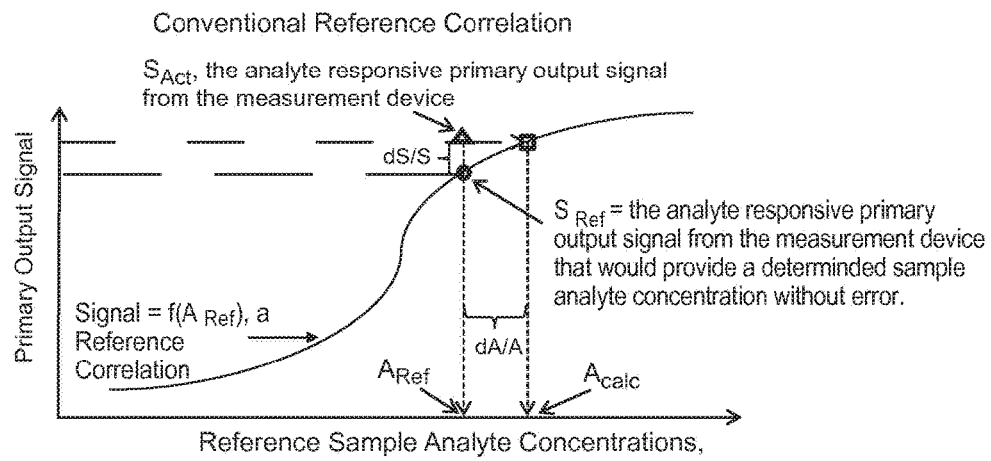
FIG. 1 is a representation of system and output signal error.

During analyte analysis, errors may be introduced into an analysis by both the biosensor system used to perform the analysis and by errors in the output signal measured by the measurement device of the biosensor. Biosensor system errors may occur from multiple sources, with an error source being in the reference correlation stored in the measurement device of the biosensor system. Thus, the laboratory determined calibration information used to convert the output signals measured by the measurement device during an analysis of a test sample into the determined analyte concentration of the sample includes error. While one might expect system errors introduced by the calibration information of the measurement device to be the same for every analysis, and thus straightforward to remove before the measurement device is used, this is not correct for all types of system errors. Some errors in the calibration information only arise under the conditions of a specific analysis, and thus cannot be removed from the calibration information without a change that would result in a system error for another specific analysis. Thus, it is difficult to remove system error for the conditions of one specific analysis without potentially adversely affecting the system error for a different specific analysis when system error arises from the calibration information. The output signal errors arise from one or more error contributors, such as the physical characteristics of the sample, the environmental aspects of the sample, the operating conditions of the system, and the manufacturing variation between test sensor lots. These output signal errors may become amplified or complicated when the signal is converted to a concentration by the calibration information.

For a reference sample, system error may be determined through the determination of relative error by subtracting the reference sample analyte concentration from the measurement device determined analyte concentration and dividing by the reference sample analyte concentration (A$_{calc}$−A$_{ref}$/A$_{ref}$). The reference sample analyte concentration of the reference samples may be determined using a reference instrument, by mixing or altering known sample analyte concentrations, and the like.

However, during an analysis of a test sample with the measurement device of the biosensor system, the reference sample analyte concentration is not known. Instead, the biosensor system performs the analysis to determine the analyte concentration in the sample to the according to the design and implementation of the measurement device. Thus, "true relative error" cannot be determined by the measurement device during an analysis as the true concentration of the analyte in the sample is not known.

A pseudo-reference concentration determined during the analysis by the measurement device may be used as a substitute for true relative error. From the analysis-determined pseudo-reference concentration, an anchor parameter may be determined and used to compensate for the system error in the analysis-determined pseudo-reference concentration. The present invention introduces the determination of a pseudo-reference concentration determined during the analysis by the measurement device as a substitute for the true relative error and uses an anchor parameter to compensate for the system error in the analysis-determined pseudo-reference concentration.

The described methods, devices, and systems may provide an improvement in measurement performance by considering both system and output signal errors when determining the final analyte concentration of the sample through the use of an anchor parameter. Both system and signal errors may be "linked" in the compensation used to determine the final analyte concentration of the sample when a signal-based anchor parameter is used. The system error also may be linked to determined analyte concentrations in the case of a concentration-based anchor parameter. Preferably, both system and output signal errors are considered by the compensation used to determine the final analyte concentration of the sample. The consideration of system error in addition to output signal error also may reduce the use of error parameters in the compensation that do not well-describe the error in the output signal.

FIG. 1 is a representation of system and output signal error.

A previously determined conventional reference correlation is represented by the "S-shaped" curve as Signal=f (A$_{ref}$). A conventional reference correlation is determined by relating reference sample analyte concentrations (horizontal X-axis) to primary output signals as determined by the measurement device (vertical Y-axis). The reference sample analyte concentration of the reference samples may be determined using a reference instrument, by mixing or altering known sample analyte concentrations, and the like.

Figure 2:
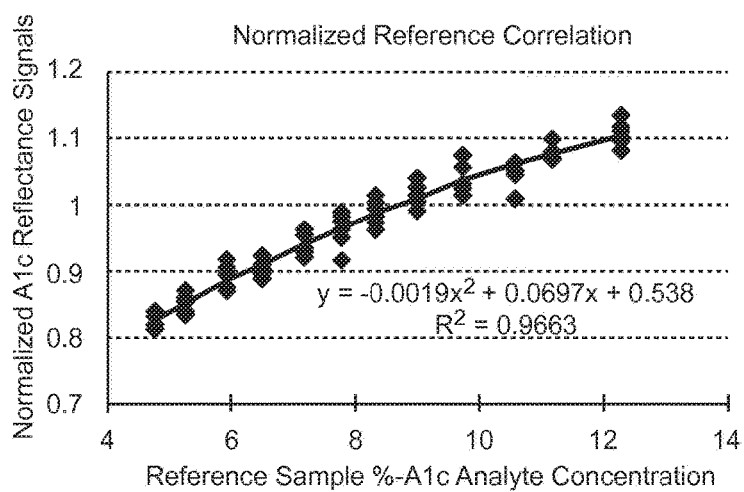
FIG. 2 provides an example of a normalized reference correlation determined for an A1c analysis system.

A conventional reference correlation between reference sample analyte concentrations and uncompensated output signal values may be represented graphically, mathematically, a combination thereof, or the like. Reference correlations may be represented by a program number (PNA) table, another look-up table, or the like that is predetermined and stored in the storage medium of the measurement device of the biosensor system. As a conventional reference correlation of this type "converts" or "translates" primary output signals from the measurement device to sample analyte concentrations, it may be referred to as a conversion relationship. A normalized reference correlation, as depicted in FIG. 2 also may be considered a conversion relationship, as it converts normalized primary output signals to sample analyte concentrations. Normalized calibration information is discussed further in relation to FIG. 7 and FIG. 11.

If error is present in the output signal measured during the analysis, the measured primary output signal as directly translated from the Y-axis through the conventional reference correlation to the horizontal X-axis of reference sample analyte concentrations will not provide the actual analyte concentration of the sample. Thus, the error in the output signal will lower the accuracy of the determined analyte concentration and decrease the measurement performance of the biosensor system.

Such an output signal measurement including error is represented in FIG. 1 by a triangle. The error in this representation increases the output signal measurement, thus shifting the position of the output signal measurement on the reference correlation. Thus, this output signal including error would be projected to the box residing on the reference correlation, as opposed to the circle, which would provide the actual analyte concentration of the sample. Thus, the reference correlation would convert the measured output signal value including error ($S_{Act}$) to the analyte concentration value $A_{calc}$. In this circumstance, the biosensor system would report $A_{calc}$ as the analyte concentration of the sample, as opposed to $A_{ref}$, due to the error in the output signal measured by the measurement device. While the error in this representation increases the output signal measurement increase the, other errors may decrease the output signal measurement or a combination of errors may increase or decrease the output signal measurement.

The error in the output signal (signal deviation dS ($S_{Act}-S_{Ref}$)) leads to an error in the determined analyte concentration of the sample (analyte concentration deviation dA ($A_{Calc}-A_{Ref}$)). The errors in the output signal or determined analyte concentration also may be expressed as a relative output signal error ($dS/S_{Ref}$) leading to a relative analyte concentration error ($dA/A_{Ref}$), where $S_{Ref}$ is the primary output signal from the measurement device that would provide a determined sample analyte concentration without error, and $A_{Ref}$ is the actual analyte concentration of the sample that should have been determined by the biosensor system. In this example, the dA and $dA/A_{Ref}$ terms represent system error, while the dS and $dS/S_{Ref}$ terms represent output signal error. While related, system and signal errors may be independent, and thus may be compensated individually or separately in addition to in combination.

Figure 3:
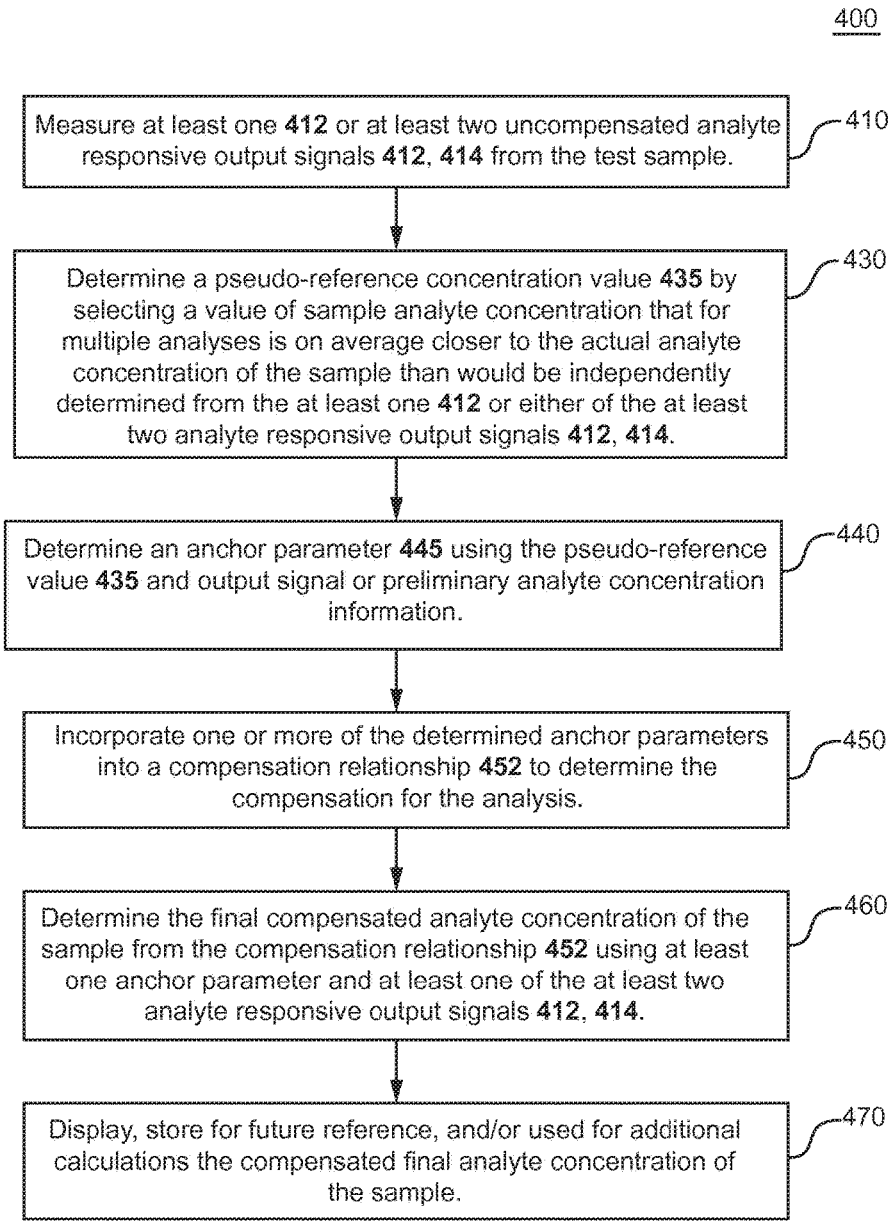
FIG. 3 represents a compensation method using an anchor parameter to compensate for system error in the final compensated analyte concentration of a sample.

FIG. 3 represents an analysis method 400 as would be implemented in the measurement device of a biosensor system using an anchor parameter to compensate for system error in the final compensated analyte concentration of a sample. The biosensor system determines the final analyte concentration of the sample from a method of error compensation including at least one anchor parameter and the output signal as measured by the measurement device. The at least one anchor parameter may be used in a method of error compensation where the conversion relationship internalizes the reduction of error arising from major error contributors, where the error from the major error contributors is reduced through primary compensation distinct from the conversion relationship, where residual compensation is used with the conversion relationship, or where the residual compensation is used with the primary compensation and the conversion relationship. The major error contributors for %-A1c analyses are temperature and total hemoglobin, while in glucose analyses the major error contributors are temperature and hematocrit. The major error contributors may be different for different types of analyte analysis.

In an analyte analysis, such as the determination of the %-A1c or glucose concentration in blood, the actual value of %-A1c or glucose in the sample is unknown. Instead, the biosensor system performs the analysis to determine the analyte concentration in the sample according to the design and implementation of the measurement device. Thus, the measurement performance of the biosensor system may be increased through compensation. The method 400 may be used in both optical and electrochemical biosensor systems to determine anchor parameter compensated sample analyte concentrations.

In analysis output signal measurement 410, at least one analyte responsive output signal 412 or preferably at least two analyte responsive output signals 412, 414 are measured from the test sample by the measurement device of the biosensor system. The at least two analyte responsive output signals 412, 414 may be independent analyte responsive output signals such as output signals generated separately by independent input signals, the independent output signals from multi-zone detectors such as the independent signals depicted in FIG. 6 of two Zone 1 detectors, and the like.

The output signals are generated from a sample of a biological fluid in response to a light-identifiable species or an oxidation/reduction (redox) reaction of the analyte. Depending on the biosensor system, these primary output signals may or may not include the effect of an extraneous stimulus. However, if one analyte responsive output signal is measured, at least one secondary output signal responsive to an extraneous stimulus that may be used for compensation also is measured. Depending on the biosensor system, the primary output signals may or may not be used to determine an initial analyte concentration for the at least one analyte responsive output signal 412 or for each of the at least two analyte responsive output signals 412, 414.

Figure 4:
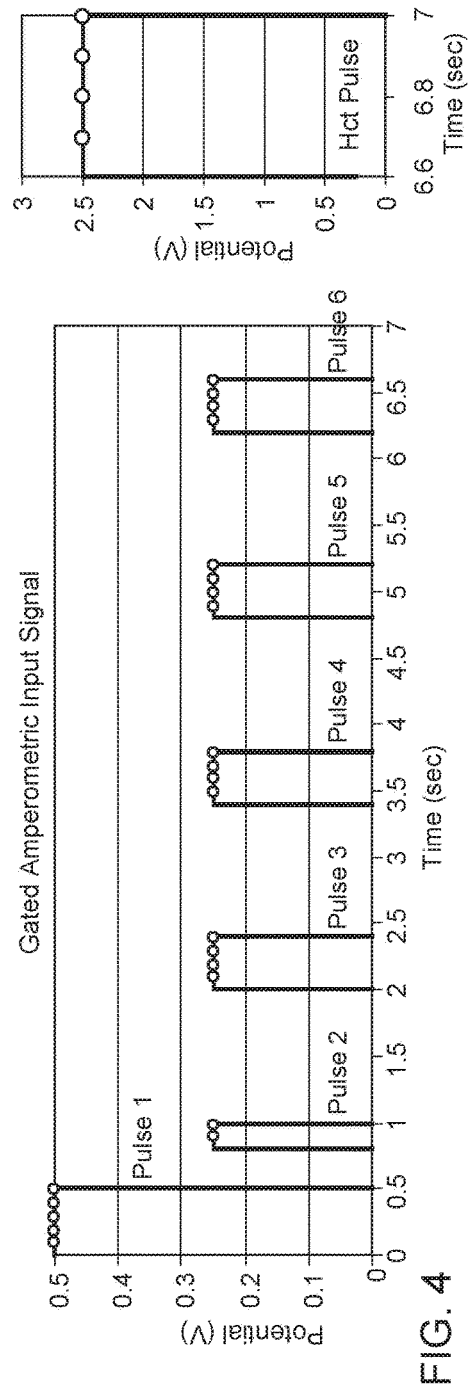
FIG. 4 depicts the input signals applied to a test sensor for an electrochemical gated amperometric analysis where six relatively short excitations are separated by five relaxations of varying duration.

FIG. 4 depicts the input signals applied to a test sensor for an electrochemical gated amperometric analysis where six relatively short excitations are separated by five relaxations of varying duration. In addition to the six excitations applied to the working and counter electrodes, a second input signal is applied to an additional electrode to generate a secondary output signal responsive to the hematocrit (Hct) concentration of the blood sample. The solid lines describe the substantially constant input potentials, while the superimposed dots indicate times of taking discrete current measurements.

Figure 5:
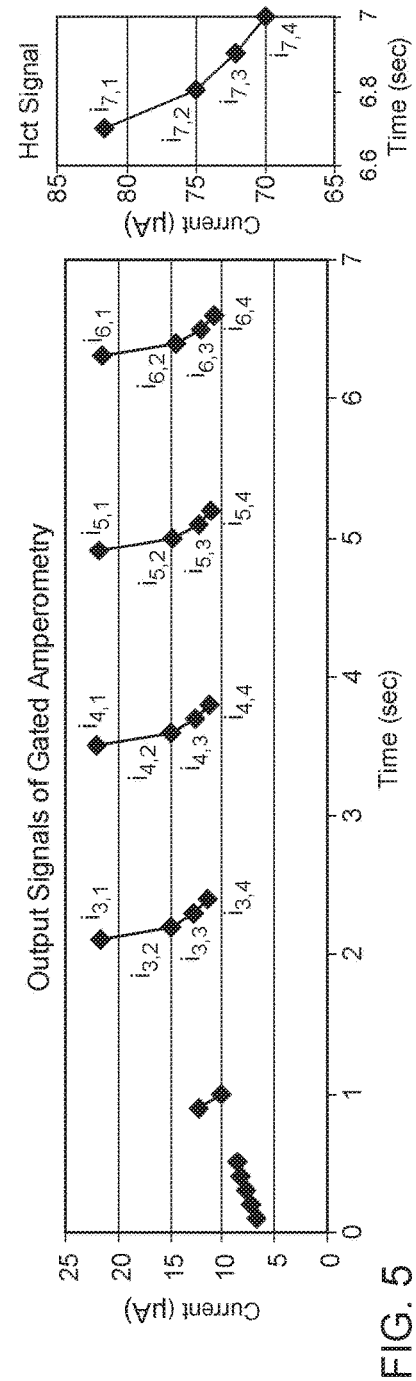
FIG. 5 depicts the primary output signals recorded from the six amperometric excitations and the secondary output signal recorded from the Hct pulse of FIG. 4.

FIG. 5 depicts the primary output signals recorded from the six amperometric excitations and the secondary output signal recorded from the Hct pulse of FIG. 4. Thus, pulses 1-6 generate primary output signals, while the Hct pulse generates a secondary output signal. FIG. 5 provides examples of analyte (e.g. glucose) responsive primary output signals and extraneous stimulus (e.g. Hct) responsive secondary output signals that may be used in the analysis output signal measurement 410.

Figure 6:
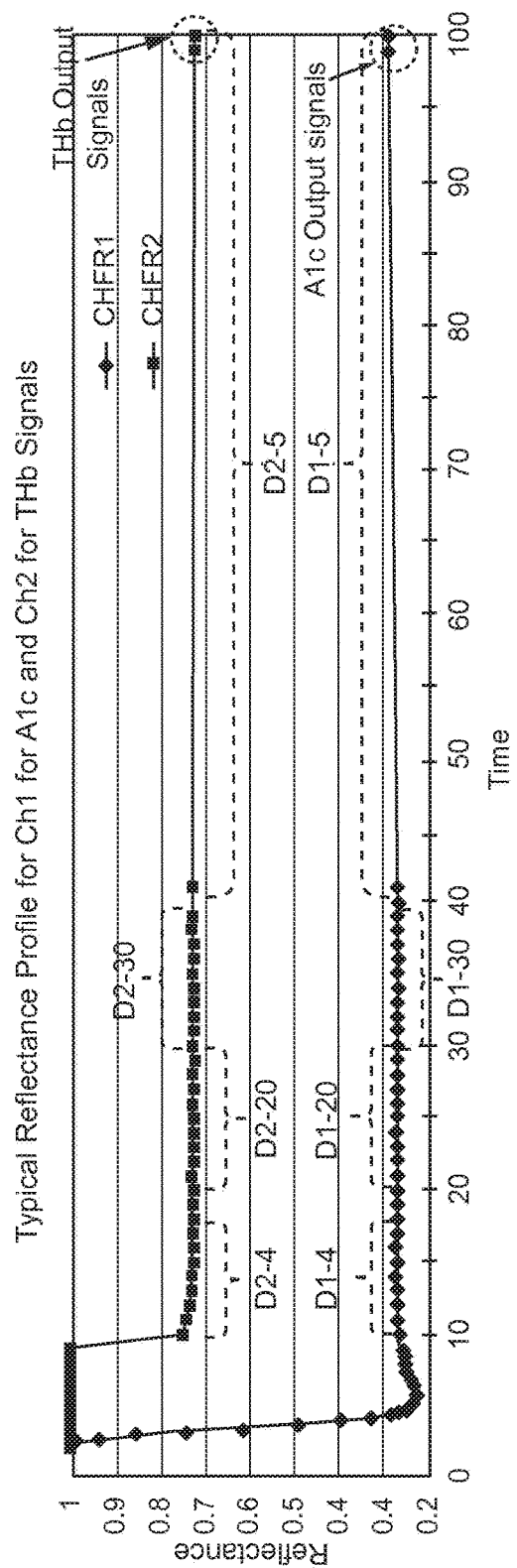
FIG. 6 depicts the output signals recorded from two of the four output channels of an A1c analysis biosensor system.

FIG. 6 depicts the output signals recorded from two of the four output channels of an A1c analysis biosensor system. The independent signals from the two Zone 1 detectors (Ch1 and Ch3 detectors) depend on the A1c concentration of the sample, but also on the THb content of the sample. The independent signals from the two Zone 2 detectors (Ch2 and Ch4 detectors) are independent of the A1c concentration of the sample, but depend on the THb concentration of the sample. The figure shows the outputs for Ch1 and Ch2. In this type of A1c system, the Zone 1 detectors provide the primary output signals while the Zone 2 detectors provide the secondary output signals. FIG. 6 provides examples of analyte responsive (e.g. A1c) output signals and extraneous stimulus (e.g. THb) responsive secondary output signals that may be used in the analysis analyte responsive output signal measurement 410.

In analysis pseudo-reference concentration value determination 430, a pseudo-reference concentration value 435 is determined. The pseudo-reference concentration value 435 is determined by determining a value of sample analyte concentration that for multiple analyses is on average closer to the actual analyte concentration of the sample than would be determined from the at least one analyte responsive output signal 412 or either of the at least two analyte responsive output signals 412, 414. Thus, the pseudo-reference is an approximation of the analyte concentration of the sample that is closer to the reference concentration on average than a concentration determined from an individual primary output signal of the measurement device.

The pseudo-reference concentration value 435 may be determined by determining an initial analyte concentration for each of the at least two analyte responsive output signals 412, 414 and averaging these initial analyte concentrations. The pseudo-reference concentration value 435 also may be determined by averaging the at least two analyte responsive output signals 412, 414 to provide an averaged signal and then converting the averaged signal into the pseudo-reference concentration value 435 from the averaged signal. The initial analyte concentrations may be determined with calibration information including a conventional reference correlation and output signals as measured by the measurement device, a normalized reference correlation and normalized output signals, or either type of calibration information in combination with additional compensation. Calibration information including a conventional reference correlation was previously discussed with regard to FIG. 1. Calibration information including the normalizing relationship and the normalized reference correlation was previously discussed with regard to FIG. 1 and is further discussed with regard to FIG. 7 and FIG. 11.

In addition to averaging initial analyte concentrations, the pseudo-reference concentration value 435 also may be determined from the at least one analyte responsive output signal 412 by using a compensation method providing on average a more accurate analyte concentration of the sample than that determined from the at least one analyte responsive output signal 412 without compensation. In this scenario, a primary compensation method is preferably used to determine the pseudo-reference concentration value 435.

Primary compensation internalized in a conversion relationship may be algebraic in nature, thus linear or non-linear algebraic equations may be used to express the relationship between the determined analyte concentration of the sample and the uncompensated output signal and error parameters. For example, in a %-A1c biosensor system, temperature (T) and total hemoglobin (THb) are the major error contributors. Similarly to hematocrit error in blood glucose analysis, different total hemoglobin contents of blood samples can result in different A1c signals erroneously leading to different A1c concentrations being determined for the same underlying A1c concentration. Thus, an algebraic equation to compensate these error may be $A1c = a_1 * S_{A1c} + a_2 / S_{A1c} + a_3 * THb + a_4 * THb^2$, where A1c is the analyte concentration after conversion of the uncompensated output values and primary compensation for total hemoglobin, $S_{A1c}$ is the temperature compensated output values (e.g. reflectance or adsorption) representing A1c, and THb is the total hemoglobin value calculated by $THb = d_0 + d_1 / S_{THh} + d_2 / S_{THb}^2 + d_3 / S_{THb}^3$, where $S_{THb}$ is the temperature corrected THb reflectance signal obtained from the test sensor. The temperature effects for $S_{A1c}$ and $S_{THb}$ may be corrected with the algebraic relationship $S_{A1c} = S_{A1c}(T) + [b_0 + b_1 * (T - T_{ref}) + b_2 * (T - T_{ref})^2]$ and $S_{THb} = [S_{THb}(T) c_0 + c_1 * (T - T_{ref})] / [c_2 * (T - T_{ref})^2]$. By algebraic substitution, the primary compensated analyte concentration A may be calculated with conversion of the uncompensated output values and primary compensation for the major error contributors of temperature and total hemoglobin being integrated into a single algebraic equation. More detail regarding primary compensation also may be found in U.S. Pat. Pub. 2011/0231105, entitled "Residual Compensation Including Underfill Error", filed Mar. 22, 2011 or in U.S. Pat. Pub. 2013/0071869, entitled "Analysis Compensation Including Segmented Signals", filed Sep. 20, 2012.

The method of determining the pseudo-reference concentration value 435 and any associated relationships is preferably pre-determined in the laboratory and stored in the storage medium of the measurement device of the biosensor system for use during the analysis of a test sample.

In analysis anchor parameter value determination 440, one or more anchor parameters are determined using the pseudo-reference concentration value 435 and the analyte responsive output signal or initial analyte concentration information. Preferably, an anchor parameter is determined for each of the at least two analyte responsive output signals 412, 414 measured from the test sample.

Figure 7:
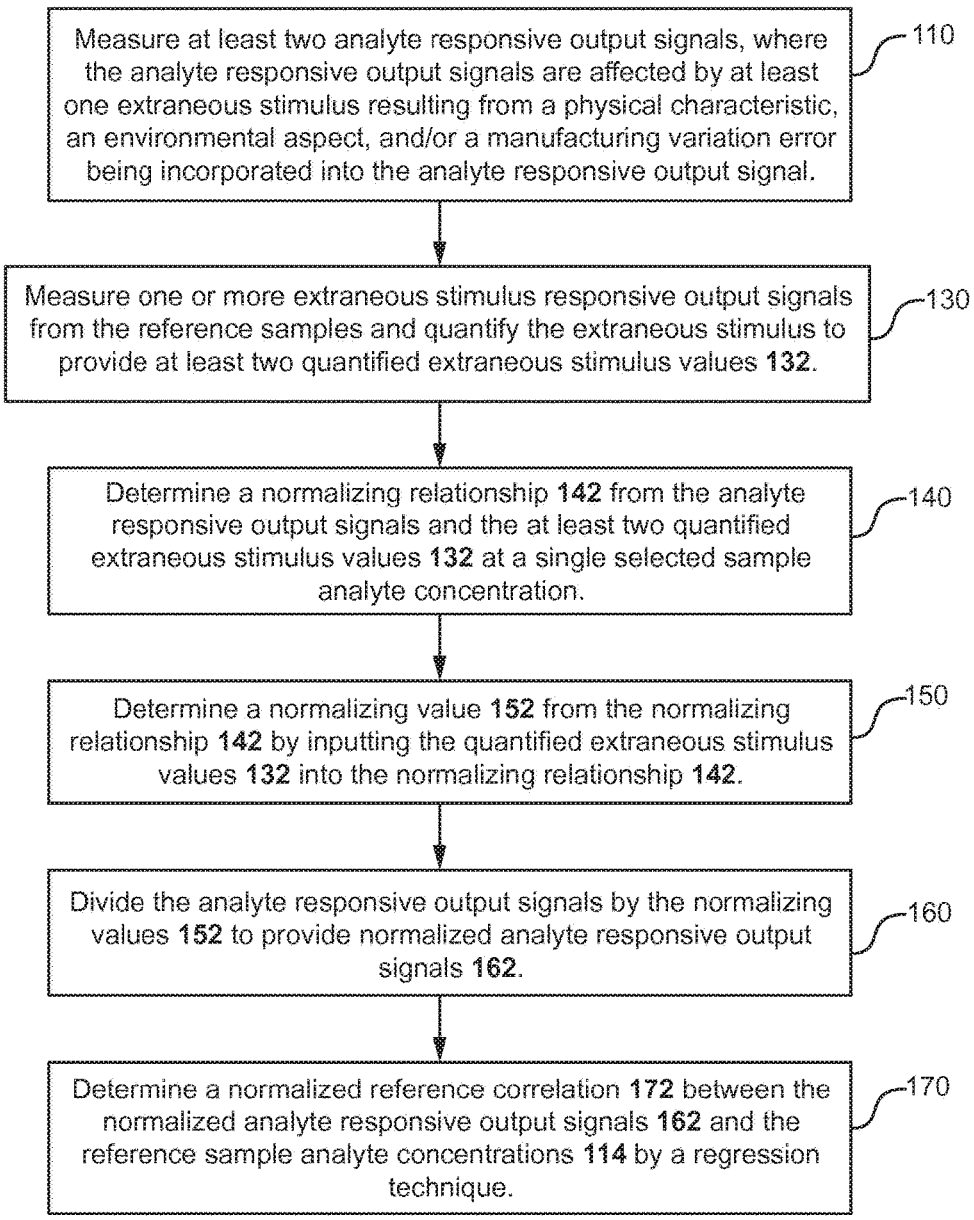
FIG. 7 represents a factory calibration method of determining calibration information through a normalization procedure.
Figure 11:
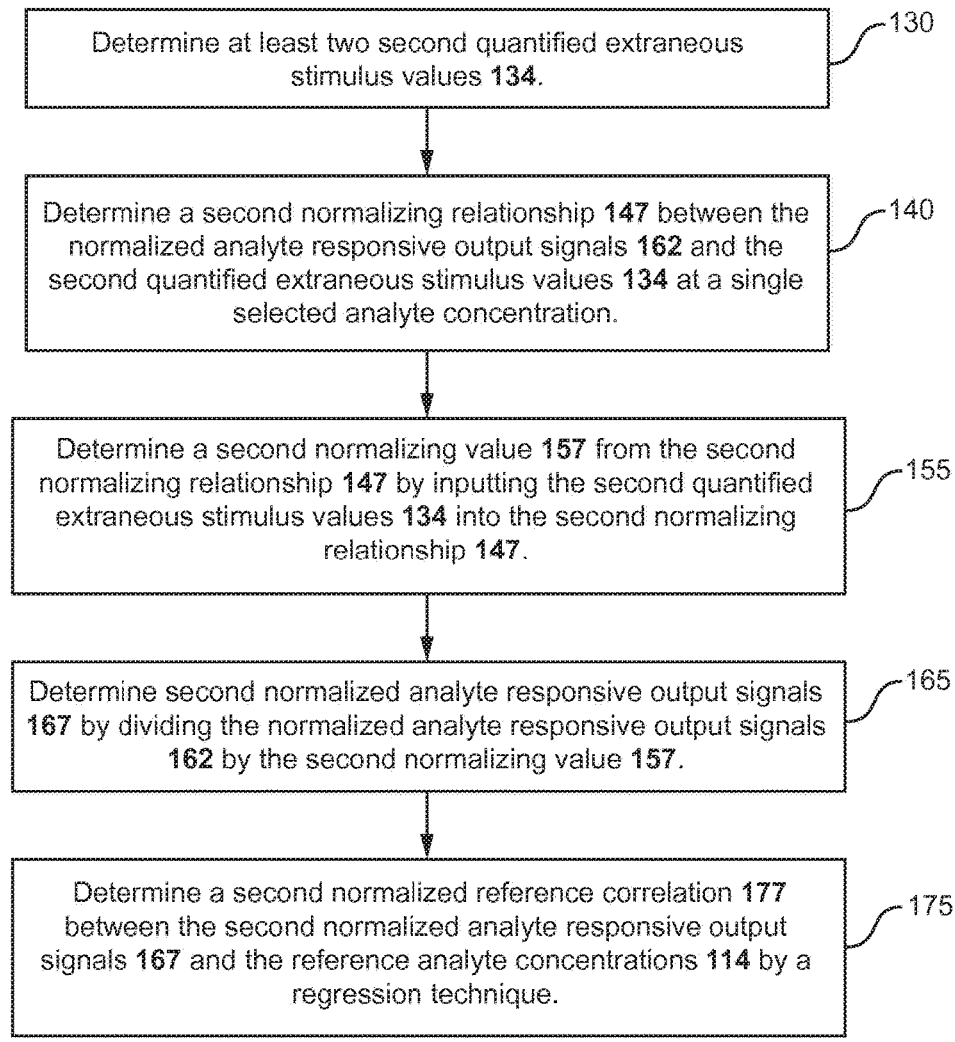
FIG. 11 represents an optional factory calibration method of also considering a second extraneous stimulus with the calibration information.
Figure 12:
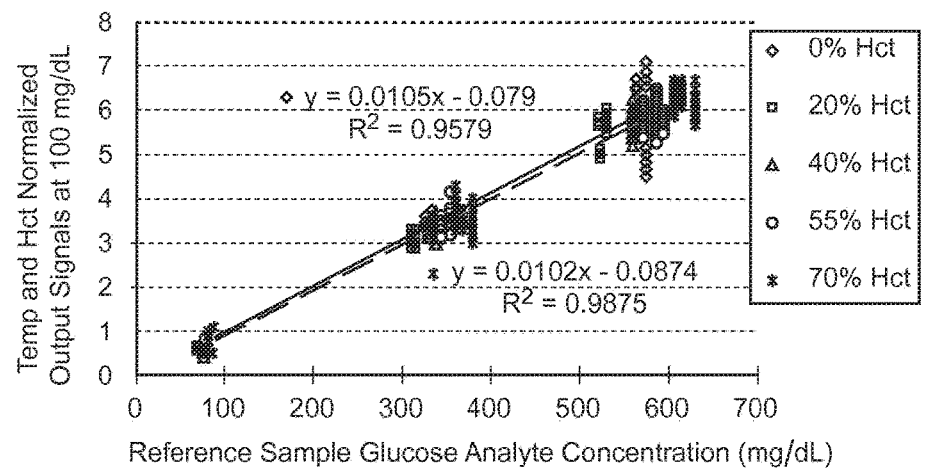
FIG. 12 provides an example of determining second normalized analyte responsive output signals in a glucose analysis system.

When the at least two analyte responsive output signals 412, 414 are used to determine the pseudo-reference concentration value 435, the measurement device preferably includes calibration information including a normalizing relationship and a normalized reference correlation, as further discussed with regard to FIG. 7 and FIG. 11. In this case, the general relationship for determining a first anchor parameter 442 may be represented as First Signal Anchor Parameter=$(NR_{OSV1} - NR_{Psuedo})/NR_{Pseudo}$, where $NR_{OSV1}$ is a first normalized output signal value determined from the first analyte responsive output signal and a normalizing relationship, and $NR_{Pseudo}$ is a pseudo-reference signal determined from the pseudo-reference concentration value 435 with a normalized reference correlation. Similarly, the general relationship for determining a second anchor parameter 444 may be represented as Second Signal Anchor Parameter=$(NR_{OSV2} - NR_{Pseudo})/NR_{Pseudo}$, where $NR_{OSV2}$ is a second normalized output signal value determined from the second analyte responsive output signal and the normalizing relationship, and $NR_{Pseudo}$ is a pseudo-reference signal value determined from the pseudo-reference concentration value 435 with the normalized reference correlation. This signal-based method of determining anchor parameters is further discussed with regard to FIG. 14.

When initial analyte concentrations determined from the at least two analyte responsive output signals 412, 414 are used in determining the pseudo-reference concentration value 435, the measurement device may include calibration information including a conventional reference correlation, as previously discussed with regard to FIG. 1, or the normalizing relationship and the normalized reference correlation (e.g. FIG. 2), as further discussed with regard to FIG. 7 and FIG. 11. In this case, the general relationship for determining a first anchor parameter 444 may be represented as First Concentration Anchor Parameter=(initial analyte concentration determined from the first output signal 412–pseudo-reference concentration value 435)/pseudo-reference concentration value 435. Similarly, the general relationship for determining a second anchor parameter 446 may be represented as Second Concentration Anchor Parameter=

(initial analyte concentration determined from the second output signal 414–pseudo-reference concentration value 435)/pseudo-reference concentration value 435. This concentration-based method of determining anchor parameters is further discussed with regard to FIG. 15. Preferably, the determined pseudo-reference concentration value is closer to the actual analyte concentration of the sample than the initially determined analyte concentration value.

When the at least one analyte responsive output signal 412 is used to determine the pseudo-reference concentration value 435 using compensation, the anchor parameter may be determined through the general relationship Concentration Anchor Parameter=(initial analyte concentration determined from the first output signal 412 without compensation–pseudo-reference concentration value 435 determined with compensation)/pseudo-reference concentration value 435 determined with compensation. While the terms "without compensation" and "with compensation" are used, "without compensation" may include compensation as long it is not the compensation used to determine the pseudo-reference concentration value 435.

In analysis compensation determination 450, one or more of the determined anchor parameters are incorporated into a compensation relationship 452 to determine the compensation for the analysis. The compensation relationship 452 provides compensation for system error.

System error may be compensated using a residual error compensation technique. Residual error may be expressed generally by Residual Error=total error observed–primary function corrected error. Of the total error in the measured output values, primary compensation removes at least 40% of the error, preferably at least 50%. Thus, in the compensated final analyte concentration of the sample, primary compensation removes from 40% to 75% of the total error, and more preferably from 50% to 85%. While error compensation provided by the anchor parameter/s may be used alone, preferably the anchor parameters are used in combination with SSP and other error parameters.

When the compensation relationship 452 is determined from multi-variant regression or similar mathematical technique, the compensation relationship 452 may compensate for error other than the system error described by the anchor parameter/s and may incorporate primary compensation with residual compensation. In these techniques, the anchor parameters, which represent system error, are combined with other error parameters, such as with segmented signal processing (SSP) parameters, cross-terms, and ratio parameters, to determine the compensation relationship 452. The determination of the compensation relationship 452 using multi-variant regression is further discussed with regard to FIG. 16. The anchor parameter/s also may be useful to compensate determined analyte concentrations in other ways.

In analysis final analyte concentration determination 460, the final compensated analyte concentration of the sample is determined from the compensation relationship 452 using at least one anchor parameter and the at least one analyte responsive output signal 412 or the at least two analyte responsive output signals 412, 414. A general expression that may be used to determine the final compensated analyte concentration of the sample may be expressed as Compensated Final Analyte Concentration=Initial analyte concentration determined without anchor parameter compensation ($A_{calc}$)/(1+RE), where RE is the compensation relationship 452. When multi-variant regression is used to determine the compensation relationship 452, the final compensated analyte concentration of the sample is determined from a linear combination of terms modified by weighing coefficients, where at least one of the terms includes an anchor parameter. The anchor parameter itself and/or a related cross-term of the anchor parameter may be used.

When the at least two analyte responsive output signals 412, 414 are used to determine the compensated final analyte concentration of the sample, the compensated analyte concentration determined from either output signal may be reported as the final analyte concentration. Preferably, however, the compensated final analyte concentration of the sample is determined by averaging the compensated analyte concentration determined for each signal.

In 470, the compensated final analyte concentration of the sample may be displayed, stored for future reference, and/or used for additional calculations.

FIG. 7 represents a factory calibration method 100 of determining calibration information through a normalization procedure. The factory calibration method 100 is preferably performed during factory calibration of the measurement device of the biosensor system.

In analyte responsive output signal measurement 110, analyte responsive output signals are measured from a reference sample, where the analyte responsive output signals are affected by an extraneous stimulus resulting from a physical characteristic, an environmental aspect, and/or a manufacturing variation error being incorporated into the analyte responsive output signals. At least two analyte responsive output signals are measured. Preferably, at least four, and more preferably at least 6 analyte responsive output signals are measured from the reference sample. Optical and/or electrochemical methods may be used to analyze the reference samples.

In extraneous stimulus quantification 130, one or more extraneous stimulus responsive output signals are measured from the reference samples or the sample environment of the reference samples and the extraneous stimulus quantified to provide at least two quantified extraneous stimulus values 132. The stimulus responsive output signals may be measured concurrently with the analyte responsive output signals or at different times. Preferably, the stimulus responsive output signals are measured concurrently with the analyte responsive output signals.

The extraneous stimulus may be directly quantified, such as when an optical detector or electrode outputs a specific voltage and/or amperage. The extraneous stimulus may be indirectly quantified, such as when a thermistor provides a specific voltage and/or amperage that is reported as a temperature in degrees Celsius, for example. The extraneous stimulus signals also may be indirectly quantified, such as when the Hct concentration of a sample is determined from a specific voltage and/or amperage measured from an Hct electrode, for example. The extraneous stimulus may be directly or indirectly quantified and then modified to provide the quantified extraneous stimulus values 132, such as when the directly or indirectly quantified extraneous stimulus value is transformed into a concentration. The quantified extraneous stimulus values 132 may be determined by averaging multiple values, such as multiple temperature readings recorded at the same target temperature. The extraneous stimulus may be quantified through other techniques.

Figure 8:
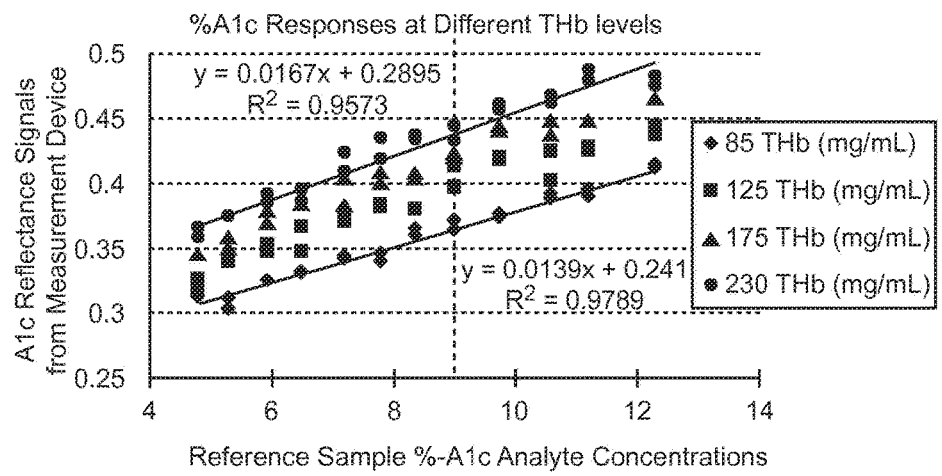
FIG. 8 shows the individual A1c reflectance signals recorded from the Zone 1 detector/s of the %-A1c measurement device separated for the four different THb concentrations in blood samples.

In normalizing relationship determination 140, a normalizing relationship 142 is determined using a regression technique from the analyte responsive output signals at a single selected analyte concentration and the quantified extraneous stimulus values 132. FIG. 8 provides an example of how a single analyte concentration was selected in an A1c analysis system and used to determine synthesized extraneous stimulus responsive output signals at the single selected analyte concentration that are responsive to the quantified extraneous stimulus signals for THb.

FIG. 8 shows the individual A1c reflectance signals recorded from the Zone 1 detector/s of the measurement device separated for the four different THb concentrations in blood samples. This allows a single sample analyte concentration to be selected from which synthesized extraneous stimulus responsive output signal values may be determined from the primary output signals. In this example, linear regression lines were determined at each of the 4 THb sample concentrations using the general relationship ($R_{A1c}$=Slope*%-A1c+Int, where $R_{A1c}$ is the output signal from the measurement device, Slope and Int are the slope and intercept, respectively of the linear regression lines at each THb sample concentration, and %-A1c is the sample analyte concentration). Other regression techniques may be used.

The regression equations determined at the 85 THb mg/mL and 230 THb mg/mL are shown on the figure, but regression equations at 127 and 175 mg/mL THb also were determined. In this example, the single selected sample analyte concentration of 9%-A1c was selected to determine the synthesized extraneous stimulus responsive output signal values from the primary output signals. Thus, in this example, the reference sample analyte concentration of 9% provided an ~0.36 A1c synthesized extraneous stimulus responsive output signal value for the 85 mg/mL THb samples from the 85 mg/mL THb regression line and an ~0.44 A1c synthesized extraneous stimulus responsive output signal value for the 230 mg/mL THb samples from the 230 mg/mL THb regression line.

Synthesized extraneous stimulus responsive output signal values can be determined in other ways than determining regression lines and "back determining" a primary output signal value from a selected reference sample analyte concentration. For example, synthesized extraneous stimulus responsive output signal values may be selected from the measured primary output signal values at one reference sample %-A1c concentration for all four THb levels. A single THb reflectance signal measured concurrently was paired with the A1c reflectance signal to form the four pairs of A1c and THb data and to construct the plot of A1c reflectance vs. THb reflectance, which will also lead to the normalizing relationship.

Thus, a synthesized extraneous stimulus responsive output signal was determined at a single selected sample analyte concentration. The synthesized extraneous stimulus responsive output signal may be thought of as the extraneous stimulus responsive output signal extracted from the combined output signal from the measurement device that includes both the primary and the extraneous stimulus. Similarly, the normalizing relationship 142 may be thought of as a reference correlation for the extraneous stimulus.

Linear or non-linear (such as polynomial) regression techniques may be used to determine the normalizing relationship 142. Linear or non-linear regression techniques include those available in the MINITAB® version 14 or version 16 statistical packages (MINTAB, INC., State College, Pa.), Microsoft Excel, or other statistical analysis packages providing regression techniques. Preferably, polynomial regression is used to determine the normalizing relationship 142. For example in MS Excel version 2010, the Linear Trendline Option accessible through the Trendline Layout Chart Tool may be selected to perform linear regression, while the Polynomial Trendline Option may be chosen to perform a non-linear polynomial regression. Other regression techniques may be used to determine the normalizing relationship 142. The normalizing relationship 142 is preferably stored in the measurement device as a portion of the calibration information.

When linear regression is used, the normalizing relationship 142 will be in the form of Y=mX+b, where m is the slope and b is the intercept of the regression line. When non-linear regression is used, the normalizing relationship 142 will be in a form of $Y=b_2*X^2+b_1*X+b_0$, and the like, where $b_2$, $b_1$ and $b_0$ are the coefficients of the polynomial. In both the linear or polynomial regression equations, Y is the calculated synthesized extraneous stimulus responsive output signal responsive to the extraneous stimulus at a single selected analyte concentration, and X is the quantified extraneous stimulus signals/values. When a value of X (the quantified extraneous stimulus signal value) is entered into either one of the relationships (linear or polynomial equations), an output value Y, representing the normalizing value (NV) is generated from the normalizing relationship.

If a second extraneous stimulus is adversely affecting the analyte responsive output signals and will be addressed by the calibration information, the normalizing relationship determination 140 is repeated for a second extraneous stimulus.

In normalizing value determination 150, a normalizing value 152 is determined from the normalizing relationship 142 by inputting the quantified extraneous stimulus values 132 into the normalizing relationship 142 and solving for the normalizing value 152.

In normalized output signal determination 160, the analyte responsive output signals are divided by the normalizing value 152 to provide normalized analyte responsive output signals 162. This preferably reduces the effect of the extraneous stimulus on the analyte responsive output signals.

Figure 9:
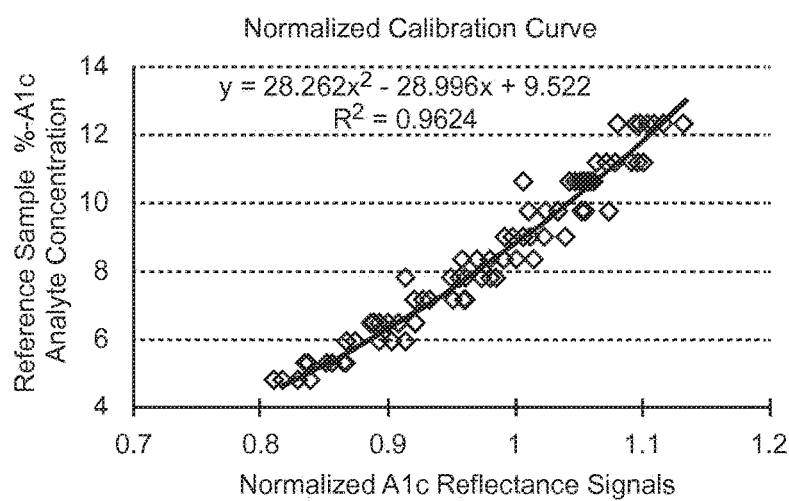
FIG. 9 represents a determined normalized reference correlation expressed as a normalized calibration curve.

In normalized reference correlation determination 170, a normalized reference correlation 172 is determined between the normalized analyte responsive output signals 162 and reference sample analyte concentrations by a regression technique. Linear or non-linear (such as polynomial) regression techniques may be used, such as those available in the MINITAB® version 14 or version 16 statistical packages (MINTAB, INC., State College, Pa.), Microsoft Excel, or another statistical analysis package providing regression techniques. Preferably, polynomial regression is used to determine the normalized reference correlation 172. For example in MS Excel version 2010, the Linear Trendline Option accessible through the Trendline Layout Chart Tool may be selected to perform linear analysis, while the Polynomial Trendline Option may be chosen to perform a non-linear polynomial analysis. Other regression techniques may be used to determine the normalized reference correlation 172. FIG. 2 provides an example of the normalized reference correlation 172, as determined for an A1c analysis system. FIG. 9 represents the determined normalized reference correlation 172 expressed as a normalized calibration curve.

When linear regression is used, the normalized reference correlation 172 will be in the form of Y=mX+b, where m is slope and b is an intercept of the regression line. When non-linear regression is used, such as a polynomial, the normalized reference correlation 172 may be in a form of $Y=b_2*X^2+b_1*X+b_0$, and the like, where $b_2$, $b_1$ and $b_0$ are the coefficients of the polynomial. The normalized reference correlation 172 is preferably stored in the measurement device as a portion of the calibration information for later use during the analysis of a sample. In the measurement device, Y is the normalized analyte responsive output signal value determined during the analysis, and X is the analyte concentration of the sample as determined from the normalized reference correlation 172. As discussed further below, for the linear normalized reference correlation, an X value (the sample analyte concentration) may be solved for when inputting a Y value (a value of the normalized output signal) into the equation. For a normalized reference correlation in the form of a $2^{nd}$ order polynomial, the normalized reference correlation 172 may be expressed in the form of a normalized calibration curve as $X=c_2*Y^2+c_1*Y+c_0$ where $c_2$, $c_1$ and $c_0$ are coefficients for the equation. A normalized output signal input to this relationship will generate an analyte concentration.

FIG. 11 represents an optional factory calibration method 102 of also considering a second extraneous stimulus with the calibration information. Thus, FIG. 7 and FIG. 11 may be combined when determining calibration information for the measurement device of the biosensor system. If a second extraneous stimulus adversely affecting the analyte responsive output signals is considered, such as the hematocrit concentration of the sample when the first extraneous stimulus is temperature, at least two second quantified extraneous stimulus values 134 may be determined in accord with the extraneous stimulus quantification 130.

Figure 10:
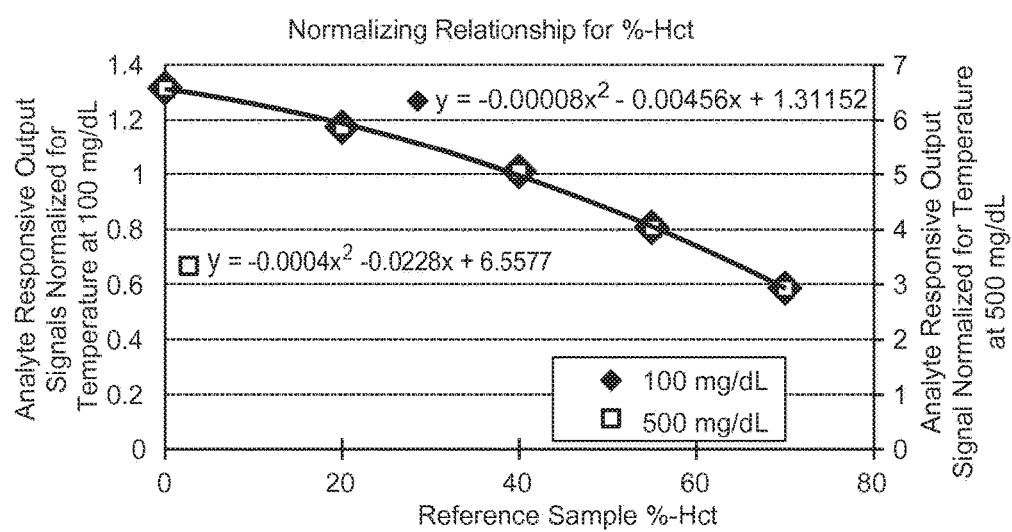
FIG. 10 provides an example of the determination of a second normalizing relationship in a glucose analysis system.

Then a second normalizing relationship 147 may be determined in accord with the normalizing relationship determination 140, but where the second normalizing relationship 147 is determined between the normalized analyte responsive output signals 162 and the second quantified extraneous stimulus at a single selected sample analyte concentration. The second normalizing relationship 147 is preferably stored in the measurement device as a portion of the calibration information. FIG. 10 provides an example of the determination of a second normalizing relationship 147 in a glucose analysis system.

In the case of the second extraneous stimulus, a second normalizing value determination 155 is performed. A second normalizing value 157 is determined from the second normalizing relationship 147 by inputting the second quantified extraneous stimulus values 134 into the second normalizing relationship 147 and solving for the second normalizing value 157.

In the case of the second extraneous stimulus, a second normalized output signal determination 165 is performed. Second normalized analyte responsive output signals 167 are determined by dividing the normalized analyte responsive output signals 162 by the second normalizing value 157. This may be thought of as making the second normalized analyte responsive output signals 167 more responsive to the reference sample analyte concentrations of the sample in relation to the analyte concentrations that would be obtained from the measurement device if the normalized analyte responsive output signals 162 were transformed by the normalized reference correlation 172. FIG. 11 provides an example of determining second normalized analyte responsive output signals 167 in a glucose analysis system.

Figure 13:
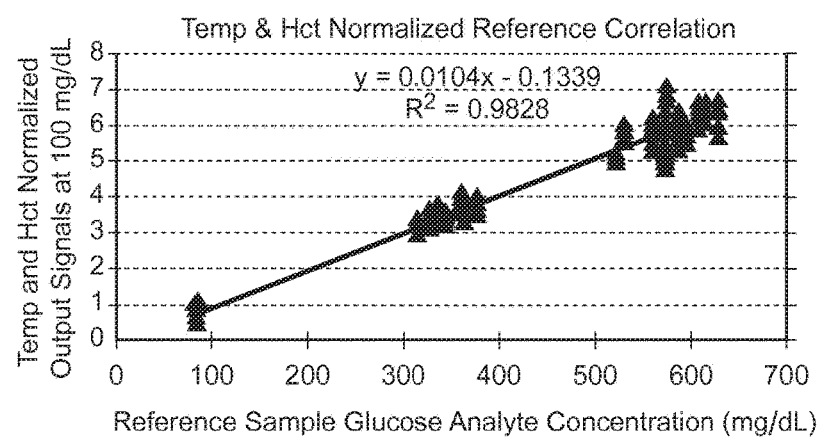
FIG. 13 provides an example of determining a second normalized reference correlation in a glucose analysis system.

In the case of the second extraneous stimulus, a second normalized reference correlation determination 175 is performed. A second normalized reference correlation 177 is determined between the second normalized analyte responsive output signals 167 and the reference sample analyte concentrations by a regression technique, as previously described. FIG. 13 provides an example of determining a second normalized reference correlation 177 in a glucose analysis system.

The second normalized reference correlation 177 is preferably stored in the measurement device as a portion of the calibration information. In this case, the normalized reference correlation 172 does not need to be stored in the measurement device and is preferably not used during the analysis. Similarly, three or more extraneous stimuli may be considered by the calibration information, where each extraneous stimulus is represented by an individual normalizing relationship stored in the measurement device in addition to a single normalized reference correlation prepared for the combined extraneous stimuli represented by the individual normalizing relationships.

Figure 14:
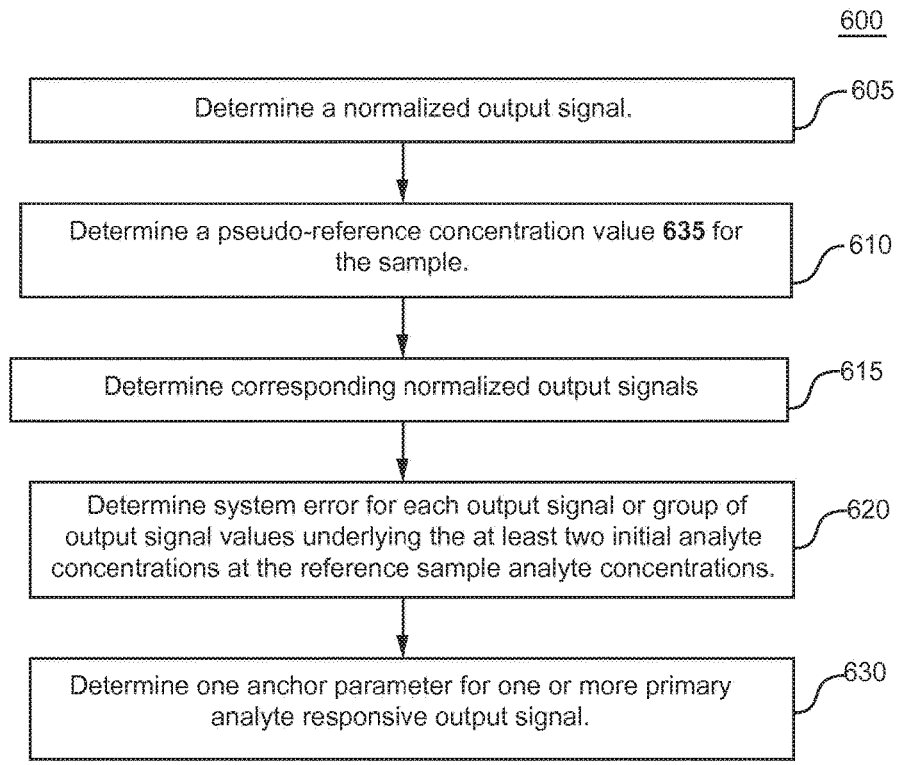
FIG. 14 represents a signal-based method of determining anchor parameters.

FIG. 14 represents a signal-based method 600 of determining anchor parameters. Anchor parameters are determined when the factory calibration information is developed for the desired output signals from the measurement device or the desired normalized output signals. An anchor parameter also is determined during the analysis by the measurement device for compensation. The measurement device includes normalization calibration information as signal-based anchor parameters are determined from the output signals. Preferably, the normalized calibration information includes at least one normalization relationship used to normalize the output signals measured by the measurement device and at least one normalized reference correlation to determine the analyte concentration of the sample from the normalized output signal values.

In 605, at least one normalized output signal ($NR_{act}$) is determined using the normalizing relationship as previously discussed with regard to FIG. 8. One or more output signals are generated by the sample using an optical and/or an electrochemical analysis. Each normalized output signal (NRact) is determined by transforming an output signal with the normalizing relationship. Thus, this is performed in the laboratory to determine the compensation relationship 452 as previously described, and during the analysis.

In 610, a pseudo-reference concentration value 635 is determined for the sample by averaging at least two initial analyte concentrations determined from the same sample. The at least two initial analyte concentrations determined from the same sample may be determined from the at least two analyte responsive output signals 412, 414. "Averaging at least two initial analyte concentrations determined from the same sample" also may include initially averaging the at least two analyte responsive output signals 412, 414 and then determining the pseudo-reference from the averaged output signals. Other output signals may be used to determine the at least two initial analyte concentrations. The at least two initial analyte concentrations may be determined in the same way for each of the at least two analyte responsive output signals 412, 414 or the initial analyte concentration determined for each of at least two analyte responsive output signals 412, 414 may be determined in different ways.

Output signals measured by the measurement device and a conventional reference correlation, normalized output signals and a normalized reference correlation, or another method may be used to determine the pseudo-reference concentration. Compensation may or may not be used to determine the initial analyte concentrations that are averaged to provide the pseudo-reference.

In 615, "corresponding normalized output signals" ($NR_{ref}$) are determined by selecting a reference sample analyte concentration from the available reference sample analyte concentrations (horizontal X-Axis) and determining the corresponding normalized output signal value (vertical Y-Axis) through the normalized reference correlation. This is similar to the "process" previously used to determine synthesized output signals with regard to FIG. 7, however instead of the regression lines be used to convert reference sample analyte concentrations to normalized output signal values, the normalized reference correlation is being used. While this process is described in the context of a graph, in practice only the reference correlation and the selected reference sample analyte concentration may be used. This process is performed in the laboratory for the desired reference sample analyte concentrations.

In 620, system error is determined for each output signal or group of output signal values underlying the at least two initial analyte concentrations at the reference sample analyte concentrations. The system error may be determined for each of the at least two initial analyte concentrations by subtracting the reference sample analyte concentration from an initial analyte concentration determined with the measurement device, and then dividing by the reference sample analyte concentration. As reference sample analyte concentrations are used to determine system error, this is a measure of relative error. This procedure can provide a system error value for each of the reference sample analyte concentrations tested in the laboratory.

The system error values arising from the reference sample analyte concentrations are then preferably used as the target system error values for determining the compensation relationship 452 established from the multi-variant regression. The compensation relationship 452 is preferably stored in the storage medium of the measurement device for use in the analysis of a sample.

In 630, at least one signal-based anchor parameter is determined for one or more primary analyte responsive output signal. Signal-based anchor parameters are determined by subtracting a pseudo-reference signal ($NR_{Pseudo}$) from the normalized output signal ($NR_{measured}$) and dividing by $NR_{Pseudo}$, thus Signal Anchor Parameter=($NR_{measured}$−$NR_{Pseudo}$)/$NR_{Pseudo}$. $NR_{Pseudo}$ is determined similarly to the "corresponding normalized output signals", except in this instance the pseudo-reference concentration is selected from the available reference sample analyte concentrations (horizontal X-Axis) and used to determine the corresponding normalized output signal value (vertical Y-Axis) through the normalized reference correlation. While this process is described in the context of a graph, in practice only the reference correlation and the selected reference sample analyte concentration may be used. This process is performed in the laboratory to determine the compensation relationship 452 as further described. This process also is performed in the measurement device using the pseudo-reference concentration value 635, as at least one anchor parameter is used in the compensation relationship 452.

Figure 15:
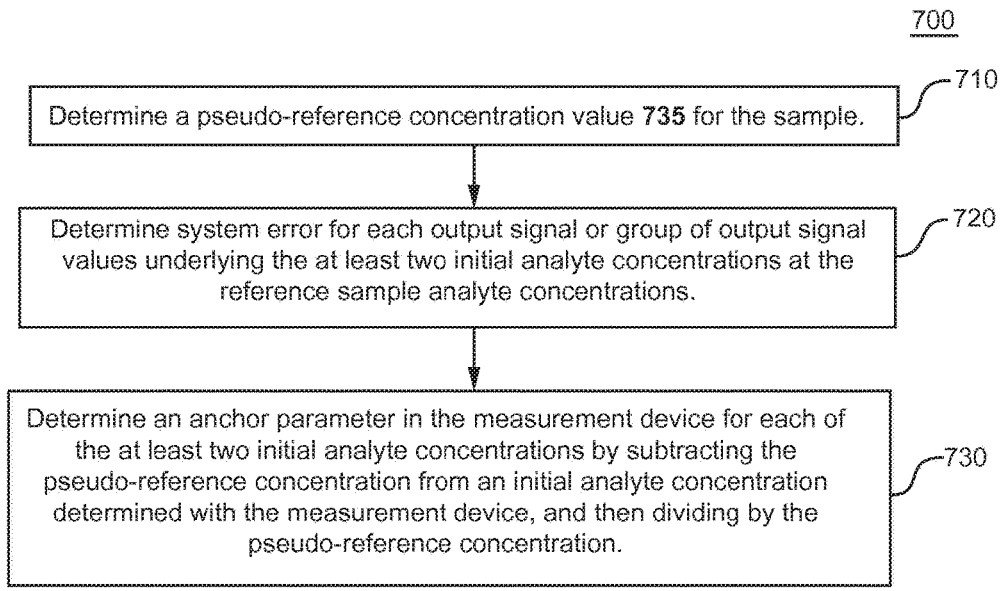
FIG. 15 represents a concentration-based method of determining anchor parameters.

FIG. 15 represents a concentration-based method 700 of determining anchor parameters as previously addressed in 440. The anchor parameters are determined during the analysis by the measurement device. While the measurement device may include normalized calibration information, it is not required as concentration-based anchor parameters are determined from initially determined sample analyte concentrations, not from the output signals.

In 710, a pseudo-reference concentration value 735 may be determined for the sample by averaging at least two initial analyte concentrations determined from the same sample as previously described for method 600. One or more output signals are generated by the sample using an optical and/or an electrochemical analysis. The at least two initial analyte concentrations are determined from the one or more output signals from the sample. Thus, the at least two initial analyte concentrations determined from the same sample may be determined from the at least two analyte responsive output signals 412, 414. "Averaging at least two initial analyte concentrations determined from the same sample" also may include initially averaging the at least two analyte responsive output signals 412, 414 and then determining the pseudo-reference from the averaged output signals. Other output signals may be used to determine the at least two initial analyte concentrations. The at least two initial analyte concentrations may be determined in the same way for each of the at least two analyte responsive output signals 412, 414 or the initial analyte concentration determined for each of the at least two analyte responsive output signals 412, 414 may be determined in different ways.

Output signals measured by the measurement device and a conventional reference correlation, normalized output signals and a normalized reference correlation, or another method may be used to determine the pseudo-reference concentration. Compensation may or may not be used to determine the initial analyte concentrations that are averaged to provide the pseudo-reference.

However, in 710, the pseudo-reference concentration value also may be determined when two initial analyte concentrations are not determined and used to determine a more accurate on average value of sample analyte concentration. In this implementation, normalized calibration information or primary compensation may be used to determine the pseudo-reference concentration value 735.

In 720, system error is determined for each output signal or group of output signal values underlying the at least two initial analyte concentrations at the reference sample analyte concentrations. The system error was determined for each of the at least two initial analyte concentration by subtracting the reference sample analyte concentration from an initial analyte concentration determined with the measurement device, and then dividing by the reference sample analyte concentration. As reference sample analyte concentrations are used to determine system error, this is a measure of relative error. This procedure can provide a system error value for each of the reference sample analyte concentrations tested in the laboratory.

The system error values arising from the reference sample analyte concentrations are then preferably used as the target system error values for determining the compensation relationship 452 established from the multi-variant regression. The compensation relationship 452 is preferably stored in the storage medium of the measurement device for use in the analysis of a sample.

In 730, a concentration-based anchor parameter is determined in the measurement device for each of the at least two initial analyte concentrations by subtracting the pseudo-reference concentration from an initial analyte concentration determined with the measurement device, and then dividing by the pseudo-reference concentration. This provides an anchor parameter for each of the initial analyte concentrations determined by the measurement device during the analysis. One or more of these anchor parameters are then provided to the previously determined compensation relationship 452 as used to provide the final analyte concentration of the sample.

In this case, the general relationship for determining a first anchor parameter 444 may be represented as First Concentration Anchor Parameter=(initial analyte concentration determined from the first output signal 412−pseudo-reference concentration value 435)/pseudo-reference concentration value 435. Similarly, the general relationship for determining a second anchor parameter 446 may be represented as Second Concentration Anchor Parameter=(initial analyte concentration determined from the second output signal 414–pseudo-reference concentration value 435/pseudo-reference concentration value 435.

Figure 16:
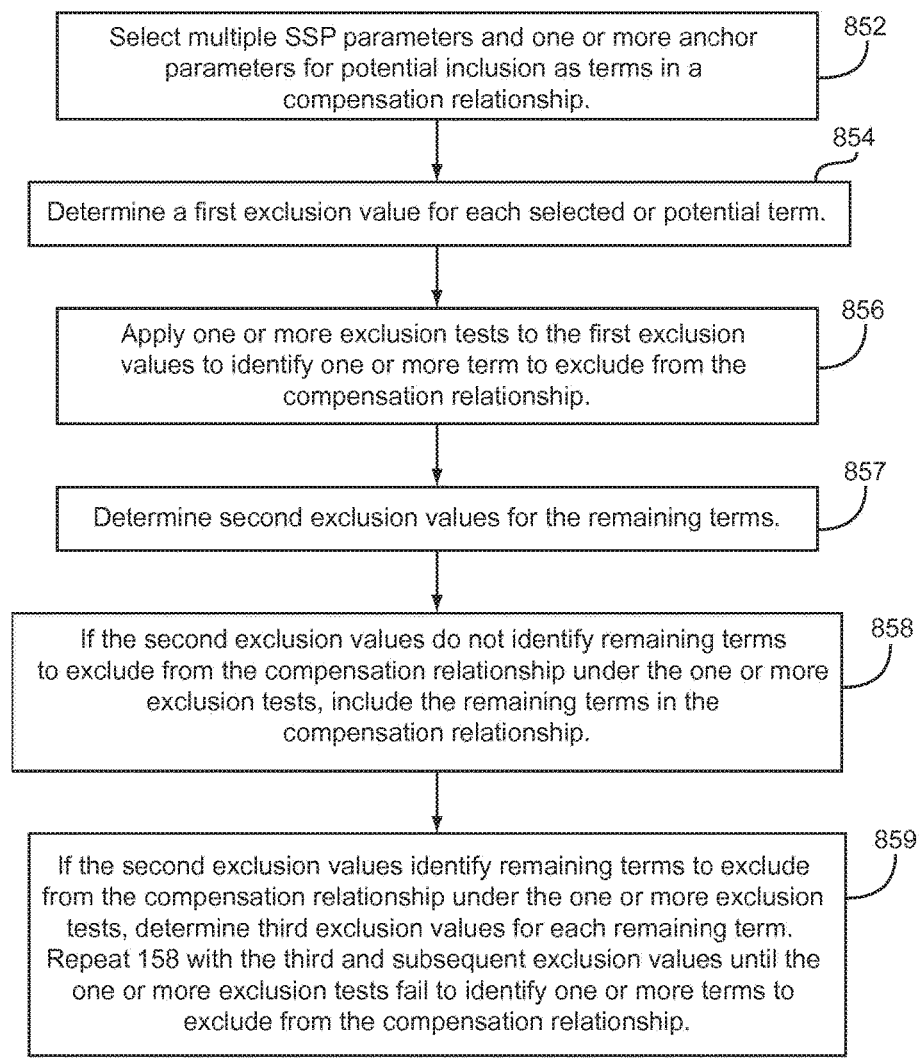
FIG. 16 represents the combination through multi-variant regression of anchor parameters with SSP parameters to determine a compensation relationship.

FIG. 16 represents the combination through multi-variant regression of anchor parameters with segmented signal processing (SSP) parameters to determine a compensation relationship between system error and analyte concentration. The compensation relationship is stored in the storage media of the measurement device of the biosensor system.

In 852, multiple SSP parameters and one or more anchor parameters are selected as terms for potential inclusion in the compensation relationship of the compensation relationship. In addition to the SSP parameters and one or more anchor parameters, other error parameters also may be included in the function, such as cross-terms, measured output signals, and quantified extraneous stimulus. As with the SSP parameters, other error parameters may be obtained from a primary output signal responsive to a light-identifiable species or from the redox reaction of an analyte in a sample of a biological fluid. The error parameters also may be obtained from a secondary output signal independent of the primary output signal, such as from a thermocouple or Hct electrode. The anchor parameters are different from these types of error parameters as the anchor parameters describe system error instead of signal error. The terms of the compensation relationship may include values other than SSP and anchor parameters, including values representing the uncompensated concentration of the analyte in the sample and the like.

Preferably, primary compensation is provided by an index function determined using error parameters from the analysis of the analyte, such as the intermediate signals from the analyte responsive output signal, or from sources independent of the analyte responsive output signal, such as thermocouples, additional electrodes, and the like. Error parameters may be responsive to one or more error contributor affecting the output signal. Thus, the error parameters may be extracted directly or indirectly from the output signal of the analysis and/or obtained independently from the analytic output signal. Other error parameters may be determined from these or other analytic or secondary output signals. Any error parameter may be used to form the term or terms that make up the index function, such as those described in Intl. Pub. No. WO 2009/108239, filed Dec. 6, 2008, entitled "Slope-Based Compensation," and the like.

An index function is responsive to at least one error parameter. An index function may generate a calculated number that correlates total analysis error to an error parameter, such as hematocrit or temperature, and represents the influence of this error parameter on bias. Index functions may be experimentally determined as a regression or other equation relating the deviation of determined analyte concentrations from a reference slope to the error parameter. Thus, the index function represents the influence of the error parameter on the slope deviation, normalized slope deviation, or percent bias arising from the total error in the analysis.

Index functions are complex when they include combinations of terms modified by term weighing coefficients. A complex index function has at least two terms, each modified by a term weighing coefficient. The combination preferably is a linear combination, but other combination methods may be used that provide weighing coefficients for the terms. For example, a complex index function may have a linear combination of terms with weighing coefficients as follows:

$f(ComplexIndex) = a1 + (a2)(R3/2) + (a3)(R4/3) + (a4)(R5/4) + (a5)(R3/2)(G) + (a6)(R4/3)(G) + (a7)(R3/2)(Temp) + (a8)(R4/3)(Temp) + (a9)(Temp) + (a10)(G) + \ldots$, where a1 is a constant and not a weighing coefficient, a2-a10 independently are term weighing coefficients, G is the determined analyte concentration of the sample without compensation, and Temp is temperature. Each of the term weighing coefficients (a2-a10) is followed by its associated term—(R3/2), (R4/3), (R5/4), (R3/2)(G), (R4/3)(G), (R3/2)(Temp), (R4/3)(Temp), (Temp), and (G). Other complex index functions may be used including nonlinear and other combinations of terms with weighing coefficients.

Each term in a complex index function may include one or more error parameters. The terms may be selected with one or more exclusion tests. More preferably, primary functions are complex index functions, such as those described in U.S. Pat. Pub. 2011/0297554, entitled "Complex Index Functions", filed Jun. 6, 2011. Other primary compensation techniques may be used.

SSP parameters are calculated from the time-based signal profiles, such as the A1c reflectance profiles or current profiles. Briefly, analysis error and the resultant bias in analyte concentrations determined from the end-point of a previously continuous output signal may be reduced by segmented signal processing (SSP) of the previously continuous output signal. By dividing the continuous output signal into segments, and converting one or more of the segments into an SSP parameter, an SSP function may be determined. Additionally, even in perturbated systems, such as those based on gated amperometry or voltammetry, segmented signal compensation can implement compensation not dependent on the perturbations arising from the gated input signal.

Cross-terms are formed by multiplying individual error parameters. For example, an uncompensated initial sample analyte concentration value and a temperature value. Ratio parameters are formed by dividing individual error parameters. For example, an uncompensated initial sample analyte concentration value and a temperature value. Intermediate currents obtained from the primary output signal at different times during the analysis also may be divided to form ratio parameters. Additional detail regarding cross-terms may be found in U.S. Pat. Pub. 2013/0071869, entitled "Analysis Compensation Including Segmented Signals", filed Sep. 20, 2012. Additional detail regarding ratio parameters may be found in U.S. Pat. Pub. 2011/0231105, entitled "Residual Compensation Including Underfill Error", filed Mar. 22, 2011.

In 854, one or more mathematical techniques are used to determine first exclusion values for each selected or potential term. The mathematical techniques may include regression techniques, preferably multi-variant regression, and the like. The exclusion values may be p-values or the like. The mathematical techniques also may provide weighing coefficients, constants, and other values relating to the selected terms. Multi-variant regression is a type of statistical regression technique that can evaluate the effect of multiple terms on a value and provide information addressing the degree to which each term affects the value. Thus, multi-variant regression can provide both weighing coefficients that address the contribution of each term and p-values addressing the terms that provide the most statistically significant contribution to the value.

MINITAB version 14 or 16 software may be used with the Multi-Variant Regression of Linear Combinations of Multiple Variables option chosen to perform the multi-variant regression. Other statistical analysis or regression options may be used to determine the weighing coefficients for the terms. Additional detail regarding multi-variant regression may be found in U.S. Pat. Pub. 2013/0071869, entitled "Analysis Compensation Including Segmented Signals", filed Sep. 20, 2012 and in U.S. Pat. Pub. 2011/0231105, entitled "Residual Compensation Including Underfill Error", filed Mar. 22, 2011.

In 856, one or more exclusion tests are applied to the exclusion values to identify one or more terms to exclude from the compensation relationship. At least one term is excluded under the test. Preferably, the one or more exclusion tests are used to remove statistically insignificant potential terms from the compensation relationship until the desired terms are obtained for the function. In 857, the one or more mathematical techniques are repeated to identify second exclusion values for the remaining terms. In 858, if the second exclusion values do not identify remaining terms for exclusion from the compensation relationship under the one or more exclusion tests, the remaining terms are included in the compensation relationship. In 859, if the second exclusion values identify remaining terms to exclude from the compensation relationship under the one or more exclusion tests, the one or more mathematical techniques of 857 may be repeated to identify third exclusion values for the remaining terms. These remaining terms may be included in the compensation relationship as in 858 or the process may be iteratively repeated as in 859 until the exclusion test fails to identify one or more terms to exclude. Additional information regarding the use of exclusion tests to determine the terms and weighing coefficients for compensation relationships may be found in U.S. Pat. Pub. 2011/0231105, filed Mar. 22, 2011, entitled "Residual Compensation Including Underfill Error".

%-A1c Analyses of Blood

Analyte concentrations were determined for multiple reference samples for Channel 1 (Ch1) and for Channel 3 (Ch3) with the measurement device to provide two initial %-A1c analyte concentrations. Thus, for each sample, a Ch1 initial analyte concentration (A1_akc) and a Ch3 initial analyte concentration (A3_$_{Calc}$) was determined. A first pseudo-reference concentration (Pseudo1) was then determined by averaging the Ch1 and Ch3 output signals and then determining the pseudo-reference concentration of each reference sample from the averaged output signal. A second pseudo-reference concentration (Pseudo2) was determined by averaging the two initial %-A1c analyte concentrations. Thus, two ways of determining a pseudo-reference concentration are described for illustration. As previously described, the pseudo-reference concentrations may be determined in other ways.

The comparison of these two techniques to the reference analyte concentration of the samples is represented in FIG. 17 through FIG. 22. The pseudo-reference concentrations (A1c_$_{Pseudo1}$) are superimposed on the known %-A1c concentrations of the reference samples (A1c_$_{Ref}$) in FIG. 17, FIG. 19, and FIG. 21. The pseudo-reference analyte concentrations determined from the averaged output signals (A1c_$_{Pseudo2}$) are superimposed on the known %-A1c concentrations of the reference samples (A1c_$_{Ref}$) in FIG. 18, FIG. 20, and FIG. 22.

Figure 17:
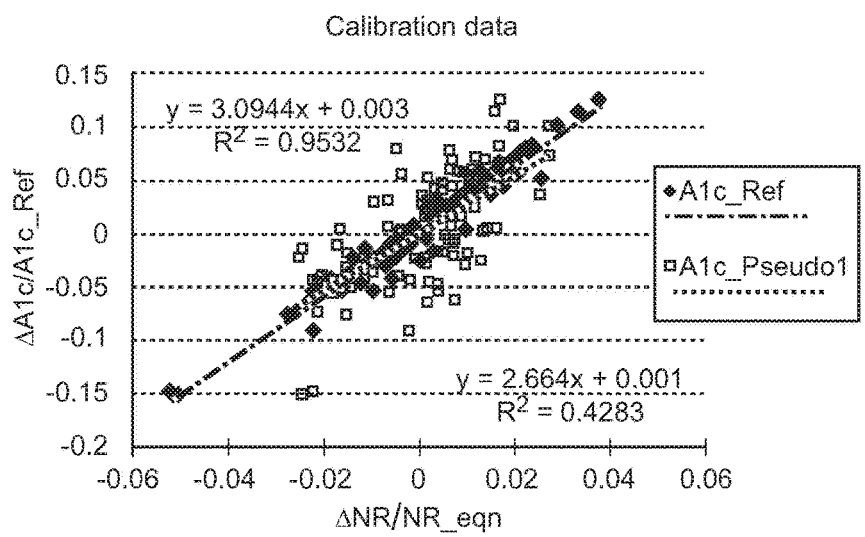
FIG. 17, FIG. 19, and FIG. 21 show the correlations between (A1c_$_{Calc}$−A1c_$_{Ref}$)/A1c_$_{Ref}$ (dA/A1c_$_{Ref}$) and (NR$_{measured}$−NR$_{Pseudo1}$)/NR$_{Pseudo1}$ (dNR/NR_$_{Pseudo1}$) using Pseudo1 as the pseudo-reference concentration.
Figure 18:
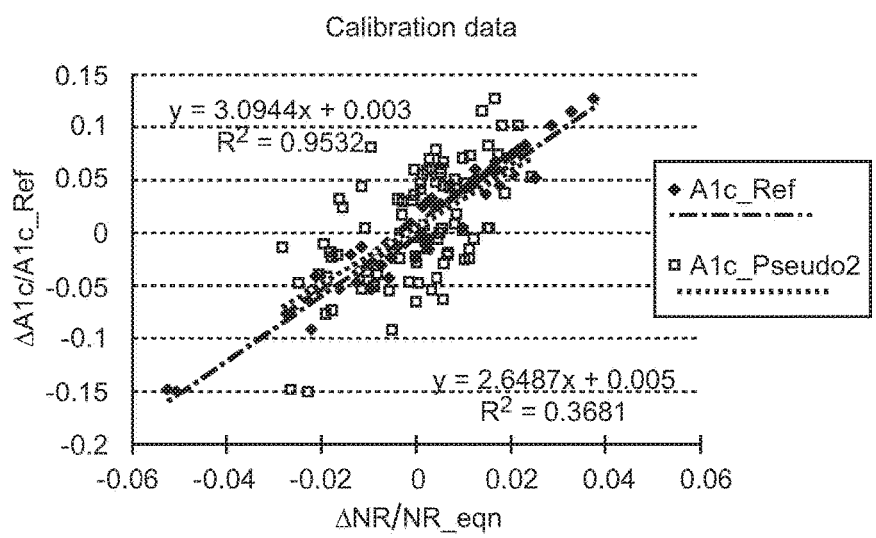
FIG. 18, FIG. 20, and FIG. 22 show the correlations for the same data, but where Pseudo2 was used as the pseudo-reference concentrations.
Figure 19:
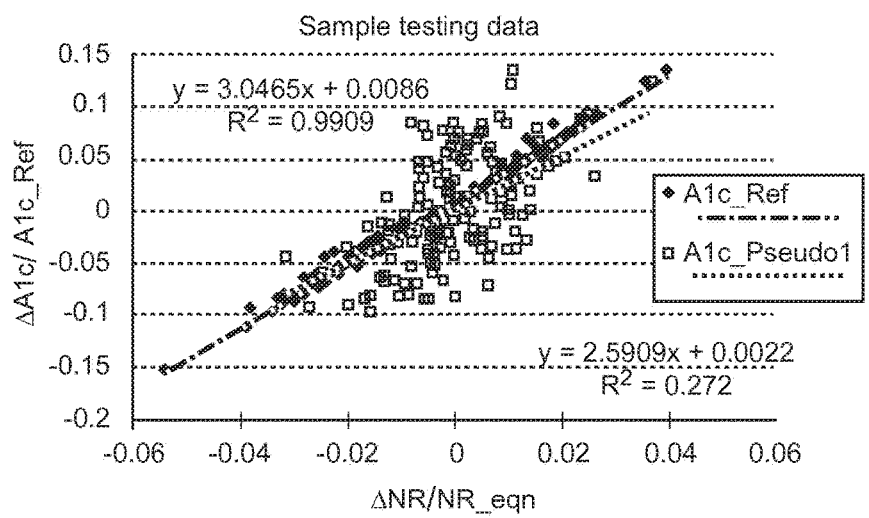
Figure 20:
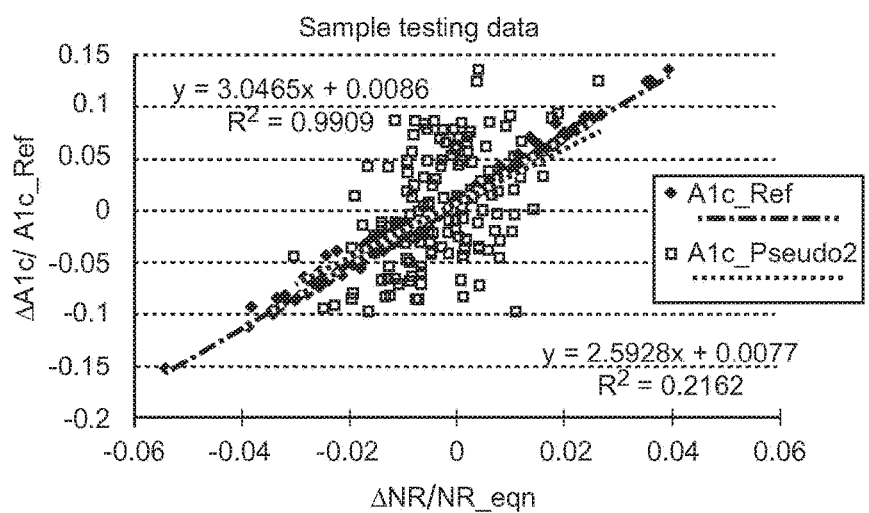
Figure 21:
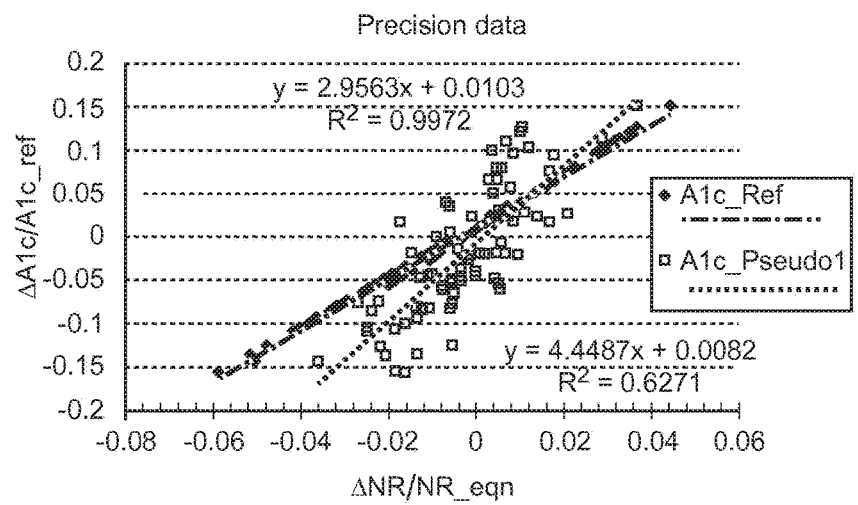
Figure 22:
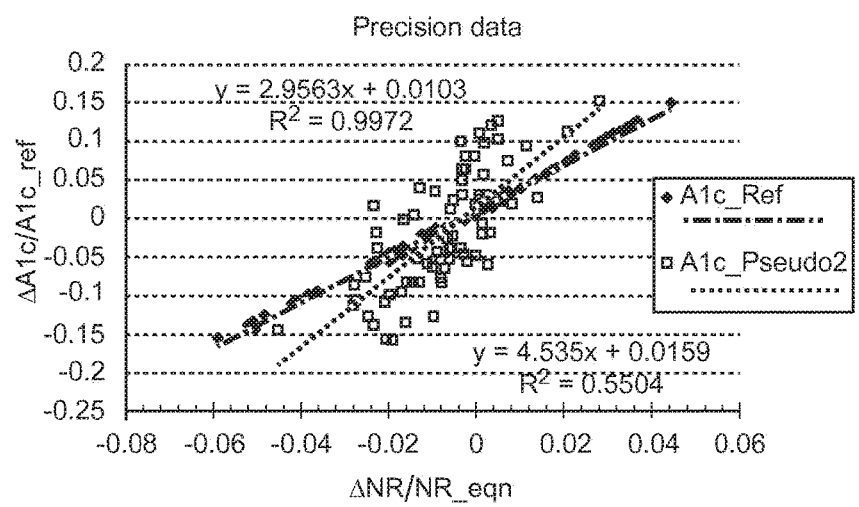

The plots of FIG. 17, FIG. 19, and FIG. 21 show the correlations between (A1c_$_{Calc}$−A1c_$_{Ref}$)/A1c_$_{Ref}$ (dA/A1c_$_{Ref}$) and (NR$_{measured}$−NR$_{Pseudo1}$)/NR$_{Pseudo1}$ (dNR/NR_$_{Pseudo1}$) using Pseudo1 as the pseudo-reference concentration. The plots were determined from the measured reflectance signals (primary output signals, reference sample analyte concentrations, normalized primary output signals, and Pseudo1-reference concentrations. The plots of FIG. 18, FIG. 20, and FIG. 22 show the correlations for the same data, but where Pseudo2 was used as the pseudo-reference concentrations. The dNR/NR_eqn relationship as used on the horizontal X-axis is an expression representing error in the normalized output signals.

For the correlations of dA/A1c_$_{Ref}$ using the reference sample analyte concentrations (A1c_$_{Ref}$), the $R^2$ correlations are approaching 1, thus indicating a near perfect correlation between the system error and the relative error, while the $R^2$ correlations of A1c_$_{Pseudo1}$ and of A1c_$_{Pseudo2}$ vary. Regardless of this variance in the $R^2$ correlations obtained by using the pseudo-reference correlations, the $R^2$ correlations for the anchor parameter determined from the pseudo-reference concentrations are significantly strong to represent the system error in the analysis.

Anchor Parameters and Residual Error Compensation

As previously discussed, anchor parameters may be used to perform residual error compensation. Residual error compensation may substantially compensate for the total error in an analysis until the error becomes random. Random error is that not attributable to any error contributor and not described by a primary or residual function at a level considered to be statistically significant.

For example, in a %-A1c analysis system, the initially determined %-A1c sample analyte concentrations are compensated with residual error compensation to provide initial sample analyte concentrations that are then averaged to provide a final analyte concentration of the sample as follows:

A1_initial (channel 1)=%-A1_initial/(1+RE1), where RE1 is the residual error function for channel 1; A3_initial (channel 3)=A3 initial/(1+RE3), where RE3 is the residual error function for channel 3; %-A1c_final=Average of A1_initial and A3_initial.

Example 1: Residual Error Compensation with Signal-Based Anchor Parameters Alone In a %-A1c analysis system, the output of linear regressions for Zone 1 channels 1 and 3 is shown in Table 1 below, where D-NA1_9 denotes the A1c relative error (A1c_$_{Calc}$−A1c_$_{Ref}$)/A1c_$_{Ref}$ for the Ch1 detector and D-NA3_9 denotes the A1c relative error (A1c_$_{Calc}$−A1c_$_{Ref}$)/A1c_$_{Ref}$ for the Ch3 detector as determined from the normalized output signals at the single selected A1c concentration of 9%. Similarly, D-(NR1) denotes the anchor parameter dNR1/NR$_{apprx}$ for channel 1 and D-(NR3) denotes the anchor parameter dNR3/NR$_{apprx}$ for channel 3. The compensation by the anchor parameter relationship (RE1=Slope*(DNR1/NR$_{apprx}$)+Int) and averaging the two A1c values provided a final standard deviation (SD) of 4.29, which was nearly equivalent to the original SD value of 4.23. The values on the "Constant" row of the regression output are not weighing coefficients, but a constant for the linear regression in the form of Y=b+m*X.

TABLE 1

Example of output linear regression, anchor parameter alone.

D-NA1_9 = 0.00348 + 2.87 D-(NR1)  
768 analyses used

| Predictor | Coef | SE Coef | T | P |
|---|---|---|---|---|
| Constant | 0.003480 | 0.001585 | 2.19 | 0.028 |
| D-(NR1) | 2.8666 | 0.1198 | 23.93 | 0.000 |

S = 0.0426028; R-Sq = 42.8%; R-Sq(adj) = 42.7%

D-NA3_9 = 0.00162 + 2.99 D-(NR3)  
768 analyses used

| Predictor | Coef | SE Coef | T | P |
|---|---|---|---|---|
| Constant | 0.001618 | 0.001603 | 1.01 | 0.313 |
| D-(NR3) | 2.9889 | 0.1190 | 25.11 | 0.000 |

S = 0.0430173; R-Sq = 45.1%; R-Sq(adj) = 45.1%

Example 2: Residual Error Compensation with Concentration-Based Anchor Parameters Alone A %-A1c analysis was performed with residual compensation using an anchor parameter determined from a pseudo-reference concentration determined from the average of two initial analyte concentrations. The %-A1c concentration determination used to provide the two initial analyte concentrations was based on a function of two input parameters: the A1c responsive primary output signals (reflectance) and the THb concentrations of the blood samples determined from the THb responsive secondary output signals. Primary compensation was used to determine the two initial analyte concentrations from the primary output signals. This method averaged the two output signals before determining the pseudo-reference concentration.

TABLE 2

Determined Mean %-Bias from Individual and Average Concentrations

|  | A1 | A3 | Aavg. | Apre-avg. |
|---|---|---|---|---|
| Mean %-bias | 3.974 | −4.920 | −0.473 | −0.082 |
| SD of %-bias | 5.997 | 4.327 | 4.1303 | 4.090 |

In Table 2, above, A1 and A3 are the %-A1c concentrations determined from Ch1 and Ch3 respectively of the %-A1c biosensor system. Aavg is the averaged concentrations of the initially determined % A1c sample concentrations determined from each of the two channels (Ch1 and Ch3) for multiple analyses. Apre-avg is the %-A1c sample analyte concentrations when the measured A1c output signals were pre-averaged before the concentration of the samples were determined.

The standard deviation (SD) values from either of the two channels of the biosensor system are larger than that of the average values of either pseudo-reference concentration determination method. Thus, the average analyte concentration values more accurately reflect the known reference sample analyte concentrations of the samples than the concentration determined from either individual channel. Thus, the %-A1c Avg or %-A1c Pre-Avg may be used as the pseudo-reference to calculate the anchor parameter.

The system error and the anchor parameters may be defined as follows in this example:

System error for each channel: $dA1/A1cRef=(A1-A1cRef)/A1cRef$; $dA3/A1cRef=(A3-A1cRef)/A1cRef$, where A1 and A3 are the initial analyte concentrations determined for each channel with primary compensation and A1cRef is the known reference sample analyte concentration of the sample. A1c was the analyte and the sample was blood. This analysis was performed in the laboratory for multiple samples having known reference sample analyte concentrations as determined with a Tosoh G7 reference instrument.

Anchor parameter for each channel: $dA1/A1cAvg=(A1-A1cAvg)/A1cAvg$; $dA3/A1cAvg=(A3-A1cAvg)/A1cAvg$, where A1cAvg is the average of the %-A1c sample analyte concentrations determined from each channel for the same test sample. Anchor parameters also could have been determined by substituting A1cAvg with A1cPre-Avg. As previously discussed, the pseudo-reference concentration may be determined in any way, as long as the pseudo-reference concentration provides a more accurate representation of sample analyte concentration for multiple analyses (thus, on average) than the initial analyte concentration/s.

In this example, system error can be generally expressed for each channel by writing system error ($dA/A1cRef$ or $dA3/A1cRef$) as a function of a concentration anchor parameter as follows: $DAr1=dA1/A1cRef=f(DA1=$anchor parameter $(dA1/A1cAvg)$ for Ch1); $DAr3=dA3/A1cRef=f$ ($DA3=$anchor parameter $(dA3/A1cAvg)$ for Ch3). These expressions were determined in the laboratory for multiple samples having known reference sample analyte concentrations as determined with a Tosoh G7 reference instrument.

An example of this method to provide a compensation relationship for use in the measurement device for analysis of a test sample based on concentration anchor parameters alone is as follows. Table 3A and Table 3C provide the analysis results of using an anchor parameter alone for compensation, while Table 3B and Table 3D provide the analysis results of using SSP and other parameters alone for compensation. The values on the "Constant" row of the linear regression output are not weighing coefficients, but a constant for the linear regression in the form of $Y=b+m*X$. The values on the "Constant" row of the multi-variant regression output are not weighing coefficients, but a constant for the multi-variant regression equation.

TABLE 3A

Example Linear Regression Equation for Ch1 Detector  
Regression Analysis: DAr1 versus DA1 - Ch1  
765 analyses performed  
DAr1 = 0.00837 + 0.944 DA1

| Predictor | Coef | SE Coef | T | P |
|---|---|---|---|---|
| Constant | 0.008368 | 0.001906 | 4.39 | 0.000 |
| DA1 | 0.94382 | 0.05379 | 17.55 | 0.000 |

S = 0.0479492  
R-Sq = 28.8%  
R-Sq(adj) = 28.7%

TABLE 3B

Example Multi-variant Regression for Ch1 Detector
Regression Analysis: DAr1 versus C2MV, MR1 - Ch1
727 analyses performed

| Predictor | Coef | SE Coef | T | P |
|---|---|---|---|---|
| Constant | −0.7465 | 0.1190 | −6.27 | 0.000 |
| C2MV | 0.5899 | 0.1511 | 3.90 | 0.000 |
| MR1 | 0.8627 | 0.2210 | 3.90 | 0.000 |
| Mt1 | −0.006734 | 0.002213 | −3.04 | 0.002 |
| D1-3a | 3.2919 | 0.5049 | 6.52 | 0.000 |
| D1-2 | −0.15905 | 0.02963 | −5.37 | 0.000 |
| D1-4/1a | 7.700 | 1.910 | 4.03 | 0.000 |
| DA1*D1-2/1 | 0.20953 | 0.02343 | 8.94 | 0.000 |
| MR1*D1-5/3a | 21.258 | 3.473 | 6.12 | 0.000 |
| Mt1*D1-4/3 | 0.009248 | 0.005813 | 1.59 | 0.112 |

S = 0.0484299
R-Sq = 30.1%
R-Sq(adj) = 29.2%

TABLE 3C

Example Linear Regression Equation for Ch3 Detector
Regression Analysis: DAr3 versus DA3 - Ch3
765 analyses performed
DAr3 = 0.00895 + 1.12 DA3

| Predictor | Coef | SE Coef | T | P |
|---|---|---|---|---|
| Constant | 0.008947 | 0.001803 | 4.96 | 0.000 |
| DA3 | 1.12349 | 0.05416 | 20.75 | 0.000 |

S = 0.0467890
R-Sq = 36.1%
R-Sq(adj) = 36.0%

TABLE 3D

Example Multi-variant Regression for Ch3 Detector
Regression Analysis: DAr3 versus C4MV, D3-2a - Ch3
727 analyses performed

| Predictor | Coef | SE Coef | T | P |
|---|---|---|---|---|
| Constant | −0.3799 | 0.1284 | −2.96 | 0.003 |
| C4MV | 0.4449 | 0.1694 | 2.63 | 0.009 |
| D3-2a | 0.6946 | 0.1738 | 4.00 | 0.000 |
| D3-3 | −2.986 | 1.004 | −2.97 | 0.003 |
| D3-5 | 295.91 | 57.83 | 5.12 | 0.000 |
| D3-3/1 | 0.05198 | 0.01432 | 3.63 | 0.000 |
| D3-3/2a | 0.0005234 | 0.0002668 | 1.96 | 0.050 |
| D3-4/2 | −1.1959 | 0.6245 | −1.91 | 0.056 |
| D3-4/3 | −5.344 | 1.189 | −4.49 | 0.000 |
| MR3*D3-2/1a | 0.8573 | 0.1320 | 6.49 | 0.000 |
| MR3*D3-4/3 | 22.757 | 5.512 | 4.13 | 0.000 |
| MR3*D3-5/3 | −18.915 | 7.914 | −2.39 | 0.017 |
| Mt3*D3-2/1a | −0.003637 | 0.001012 | −3.59 | 0.000 |
| Mt3*D3-4/2a | −0.0017349 | 0.0008277 | −2.10 | 0.036 |

S = 0.0532793
R-Sq = 20.4%
R-Sq(adj) = 18.9%

The Ch1 anchor parameter determined in Table 3A was able to describe 28.7% of the error in the determined analyte concentrations, while SSP and other parameters without the anchor parameter were able to describe 29.2% of the error in Table 3B. The Ch3 anchor parameter determined in Table 3C was able to describe 36% of the error in the determined analyte concentrations, while SSP and other parameters without the anchor parameter were able to describe 18.9% of the error in Table 3D. Thus, the anchor parameter alone was able to equal the SSP and other parameter compensation for Ch1, but was shown superior for compensating Ch3. This variability between channels shows how the ability to compensate system error during a specific analysis can provide a significant increase in the measurement performance of the biosensor system.

Example 3A: Compensation Relationship Including Signal-Based Anchor Parameters and Other Parameters The anchor parameters may be used in combination with segmented signal (SSP) and other parameters to provide the compensation relationship. Adding the anchor parameter to the multi-variant regression to determine the residual error function may increase the correlation between the system error and the compensation relationship and improve the %-A1c measurement performance of the biosensor system. Since the anchor parameter $(NR_{meaured}-NR_{pseudo})/NR_{pseudo}$ provided a relatively strong correlation with the A1c system error ($R^2$ correlation values from ~0.3-0.6), adding other terms to the compensation relationship, such as the SSP parameters, was found to improve the ability of the compensation relationship to describe the system error in the analysis than when either the anchor parameter or the SSP parameters were used alone.

Figure 23:
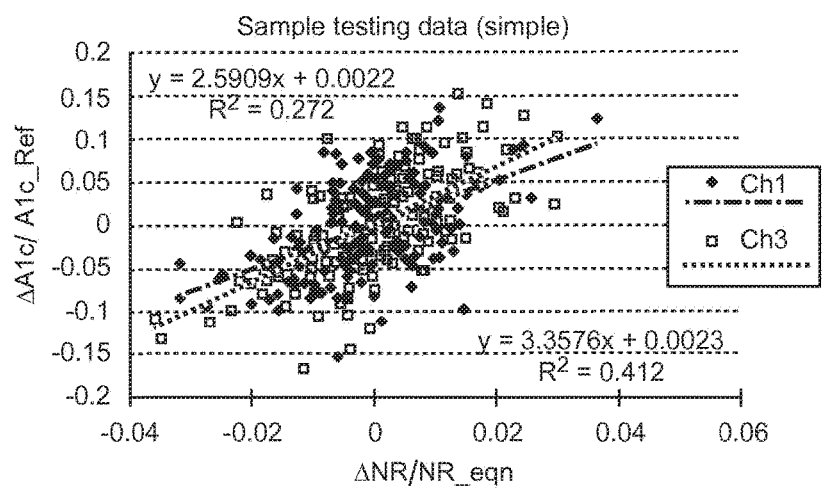
FIG. 23 provides the analysis results of using an anchor parameter alone for compensation.
Figure 24:
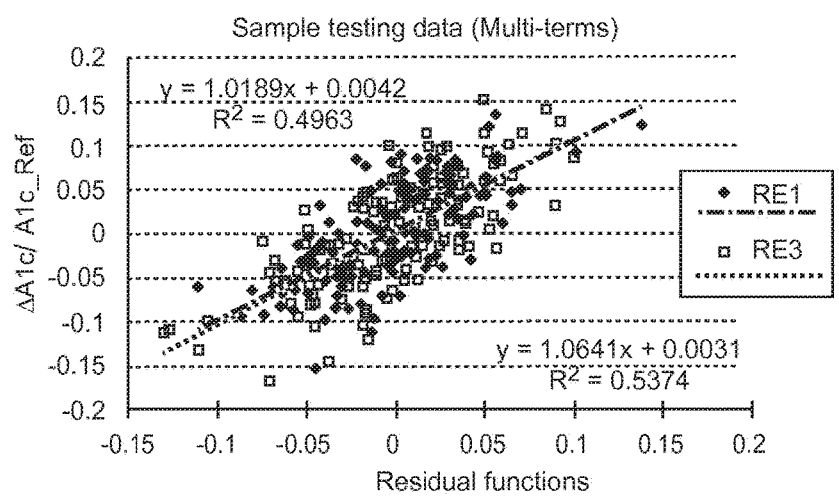
FIG. 24 provides the analysis results of using SSP and other parameters alone for compensation.

The correlation plots in FIG. 23 and FIG. 24 compare the correlations from anchor parameters alone used in the compensation relationship for residual compensation (FIG. 23) and from anchor parameters used in combination with other types of parameters including SSP parameters, cross-terms, and ratio parameters in the compensation relationship for residual compensation (FIG. 24). Multi-variant regression was used to combine, select, and weigh the parameters for inclusion in the compensation relationship. For the Ch1 detector of zone 1, the $R^2$ correlation value increased from 0.272 for the anchor parameter alone to 0.4963 for the anchor and other parameter residual function. For the Ch3 detector of zone 1, the $R^2$ correlation value increased from 0.412 for the anchor parameter alone to 0.5374 for the anchor and other parameter residual function. Thus, an increase in measurement performance of the biosensor system was observed when anchor parameters were used in combination with other parameters to determine the compensation relationship. Additional improvement in measurement performance for the biosensor system may be obtained from the averaging of the two channel %-A1c initial analyte concentrations determined with the compensation relationship including the anchor parameter.

Multi-variant regression was used to determine a compensation relationship including system error compensation provided by a signal-based anchor parameter (and associated cross-terms) for Ch1 and Ch3 of a %/-A1c biosensor system are as follows:

For Ch1 (D-NA1_9)=−0.7729+0.8349*'C2MV'+0.6484*'MR1'−0.005598*'Mt1'+0.7585*'D1-3'+53.16*'D1-5'+16.632*'D2-4'+288.14*'D2-5'+53.16*'D2-20'+0.12334*'D-C2*A1'+4.7018*'DNR1*C2MV'+2.5883*'DNR1*D1-1'−0.019564*'D1-2/1'+0.17053*'D1-2/1a'+3.737*'D1-4/1a'+1.6629*'D1-5/3a'+155.92*'DNR1*D1-4/1'+10.458*'DNR1*D1-4/3'.

For Ch3 (D-NA3_9)=−0.7167+0.8591*'C4MV'+0.6088*'MR3'−1.3598*'D3-3'+115.73*'D3-5'+20.958*'D4-4'+204.24*'D4-5'+72.19*'D4-20'+0.27735*'DNR3*A3'−0.3709*'D-C4*A3'−1.453*'DNR3*D3-1'−503.4*'D-C4*D4-4'+4469*'D-C4*D4-20'+0.0916*'D3-2/1a'+1.0911*'D3-4/1'−2.984*'D3-5/3'+1.1017*'D3-5/3a'.

For both compensation relationships, terms such as C4MV are measured reflectance; MR1 is the minimum A1c reflectance measured for an A1c reflectance profile; Mt1 is the analysis time required to reach MR1; terms such as D1-3 are SSP parameters; DNR1 is the anchor parameter for Ch1 and DNR3 is the anchor parameter for Ch3; and terms such as D1-2/1 and D1-2/1a are SSP ratio parameters from Ch1, where D1-2/1 is D1-2/D1-1 and D1-2/1a follows D1-2/D1-1 in time. FIG. 6 represents the portions of the reflectance signal corresponding to SSP parameters for Ch1 (primary output signal) and Ch2 (secondary output signal). The constant is −0.7729 for the Ch1 equation and −0.7167 for the Ch3 equation. The weighing coefficients for each term also are shown. The constant, weighing coefficients, and terms would be different for a different analysis. While one would consider both channels of the measurement device to be "the same", from the terms in the equation as determined through the exclusion process, as previously discussed, the compensation relationship is different for each channel.

The regression output from the multi-variant regression, as performed with MINITAB version 16 software using the Multi-Variant Regression of Linear Combinations of Multiple Variables option is as follows in Table 4. The values on the "Constant" row of the regression output are not weighing coefficients, but a constant for the multi-variant regression equation.

TABLE 4

| Predictor | Coef | SE Coef | T | P |
|---|---|---|---|---|
| A: Ch1 Example of Multi-variant Regression with Anchor and Other Parameters. Ch1 - 727 Analyses | | | | |
| Constant | −0.7729 | 0.1194 | −6.47 | 0.000 |
| C2MV | 0.8349 | 0.1434 | 5.82 | 0.000 |
| MR1 | 0.6484 | 0.1978 | 3.28 | 0.001 |
| Mt1 | −0.005598 | 0.001916 | −2.92 | 0.004 |
| D1-3 | 0.7585 | 0.3392 | 2.24 | 0.026 |
| D1-5 | 53.16 | 27.27 | 1.95 | 0.052 |
| D2-4 | 16.632 | 2.484 | 6.70 | 0.000 |
| D2-5 | 288.14 | 43.60 | 6.61 | 0.000 |
| D2-20 | 53.22 | 11.15 | 4.77 | 0.000 |
| D-C2*A1 | 0.12334 | 0.06338 | 1.95 | 0.052 |
| DNR1*C2MV | 4.7018 | 0.5796 | 8.11 | 0.000 |
| DNR1*D1-1 | 2.5883 | 0.8588 | 3.01 | 0.003 |
| D1-2/1 | −0.019564 | 0.005439 | −3.60 | 0.000 |
| D1-2/1a | 0.17053 | 0.02668 | 6.39 | 0.000 |

TABLE 4-continued

| Predictor | Coef | SE Coef | T | P |
|---|---|---|---|---|
| D1-4/1a | 3.737 | 1.060 | 3.52 | 0.000 |
| D1-5/3a | 1.6629 | 0.5260 | 3.16 | 0.002 |
| DNR1*D1-4/1 | 155.92 | 36.32 | 4.29 | 0.000 |
| DNR1*D1-4/3 | 10.458 | 5.344 | 1.96 | 0.051 |
| S = 0.0390445; R-Sq = 54.0%; R-Sq(adj) = 52.9% | | | | |
| B: Ch3 Example of Multi-variant Regression with Anchor and Other Parameters. Ch3 - 727 Analyses | | | | |
| Constant | −0.7167 | 0.1173 | −6.11 | 0.000 |
| C4MV | 0.8591 | 0.1547 | 5.55 | 0.000 |
| MR3 | 0.6088 | 0.1866 | 3.26 | 0.001 |
| D3-3 | −1.3598 | 0.7734 | −1.76 | 0.079 |
| D3-5 | 115.73 | 45.47 | 2.55 | 0.011 |
| D4-4 | 20.958 | 2.761 | 7.59 | 0.000 |
| D4-5 | 204.24 | 43.78 | 4.66 | 0.000 |
| D4-20 | 72.19 | 12.49 | 5.78 | 0.000 |
| DNR3*A3 | 0.27735 | 0.03963 | 7.00 | 0.000 |
| D-C4*A3 | −0.3709 | 0.1163 | −3.19 | 0.001 |
| DNR3*D3-1 | −1.4530 | 0.5336 | −2.72 | 0.007 |
| D-C4*D4-4 | −503.4 | 221.3 | −2.28 | 0.023 |
| D-C4*D4-20 | 4469 | 2452 | 1.82 | 0.069 |
| D3-2/1a | 0.09160 | 0.01080 | 8.48 | 0.000 |
| D3-4/1 | 1.0911 | 0.2548 | 4.28 | 0.000 |
| D3-5/3 | −2.984 | 1.310 | −2.28 | 0.023 |
| D3-5/3a | 1.1017 | 0.3882 | 2.84 | 0.005 |
| S = 0.0395936; R-Sq = 55.7%; R-Sq(adj) = 54.8% | | | | |

Table 5A, below, summarizes the compensation results for five lots of A1c test sensors as determined with the measurement device of a %-A1c analysis biosensor system, along with the results from a conventional analysis method using measured output signals and primary compensation to compensate for temperature and the THb concentration in the blood samples. This conventional analysis method averages the A1c reflectance signals from the Zone 1 detectors (Ch1 and Ch3), averages the THb reflectance signals from the Zone 3 detectors (Ch2 and Ch4), determines the THb concentration of the sample, and uses a two parameter function including the averaged A1c reflectance and the determined THb value to determine the %-A1c concentration of the blood sample.

TABLE 5A

| | Error in Determined Sample Analyte Concentrations | | | | | | |
|---|---|---|---|---|---|---|---|
| Analysis | Measurement Performance | Lot #1 | Lot #2 | Lot #3 | Lot #4 | Lot #5 | Overall |
| Conventional | Mean, %-bias | 0.693 | −0.725 | −0.482 | 0.316 | −0.547 | −0.149 |
| Comp, Anchor Only | Mean, %-bias | 0.783 | −0.489 | −0.018 | 0.216 | −0.514 | −0.004 |
| Comp, Anchor + SSP | Mean, %-bias | 0.133 | −0.141 | 0.202 | 0.036 | −0.221 | 0.002 |
| Conventional | SD, %-bias | 3.823 | 4.290 | 4.783 | 3.996 | 4.105 | 4.21 |
| Comp, Anchor Only | SD, %-bias | 3.788 | 4.264 | 4.704 | 4.032 | 4.265 | 4.22 |
| Comp, Anchor + SSP | SD, %-bias | 3.472 | 3.994 | 4.115 | 3.639 | 3.486 | 3.75 |
| Conventional | %-within ±7% | 95.0 | 87.6 | 85.7 | 91.6 | 92.8 | 90.5 |
| Comp, Anchor Only | %-within ±7% | 94.3 | 89.5 | 86.5 | 91.6 | 90.1 | 90.4 |
| Comp, Anchor + SSP | %-within ±7% | 95.7 | 92.5 | 91.8 | 94.2 | 93.4 | 93.5 |

For %-A1c measurements, 37 determined analyte concentrations out of 40 blood samples analyzed are preferably within ±7% from the %-A1c concentration determined for the samples with a reference instrument. Thus, preferably, 92.5% of the analyte concentrations determined by the measurement device are within ±7% of the reference instrument determined concentrations. The best results were obtained from the method of combining the anchor and other parameters in the compensation relationship, which is especially reflected in the standard deviation (SD) values of the A1c %-biases. The anchor plus SSP and other parameter compensation relationship provided an approximately 11% (4.21−3.75/4.21*100) reduction in SD in comparison to either the primary compensation or the anchor parameter compensation alone. Thus, the anchor parameter in combination with SSP and other parameters provided a substantial increase in measurement performance to the biosensor system, especially when multiple analyses are considered.

Example 3B: Compensation Relationship Including Signal-Based Anchor Parameters, Other Parameters, and an Extraneous Stimulus Anchor Parameter If an extraneous stimulus affects the primary output signal of the biosensor system and a secondary output signal is measured that is responsive to the extraneous stimulus, an anchor parameter also may be determined for the extraneous stimulus and included in determination of the compensation relationship through multi-variant regression. Thus, an extraneous stimulus signal-based anchor parameter may be thought of as describing the system error surrounding the quantification by the measurement device of the extraneous stimulus.

The same basic method 400 was followed as previously described with regard to FIG. 3, except that the anchor parameter is determined for the extraneous stimulus as opposed to the analyte. In this example, an anchor parameter was determined for the extraneous stimulus arising from THb in a %-A1c biosensor system. Anchor parameters may be determined for other extraneous stimuli, dependent on the biosensor system.

In the %-A1c biosensor system, Ch2 and Ch4 provide a THb responsive secondary output signal. Thus, a THb anchor parameter was determined through the general expression: $dR2/R_{THb\_pseudo} = (R2 - R_{THb\_pseudo})/R_{THb\_pseudo} - 1$, where R2 is the secondary output signal determined from Ch2 of the measurement device responsive to THb, and $R_{THb\_pseudo} = b2*THb_{pseudo}^2 + b_1*THb_{pseudo} + b_0$. Thus, $R_{THb\_pseudo}$ was determined by averaging an initial THb concentration determined from each of Ch2 and Ch4, or by averaging the secondary output signals from Ch2 and Ch4 and determining the concentration. Thus, a better on average THb concentration was determined than obtainable from either channel of the measurement device. This process was comparable to determining the initial analyte concentrations of the sample, but was used in this instance for the THb extraneous stimulus. This relationship would be stored in the storage media of the measurement device for use during an analysis to determine an anchor parameter for the extraneous stimulus THb.

The $THb_{pseudo}$ concentration was determined by averaging initial extraneous stimulus (THb) sample concentrations. Such a method was previously discussed in the context of the analyte with regard to 610 and 710, for example. Here, instead of the analyte responsive primary output signals, the extraneous stimulus secondary output signals were used to determine an averaged extraneous stimulus pseudo-reference concentration.

The conversion relationship for the extraneous stimulus THb used in this example was determined using non-linear, polynomial regression. Linear or non-linear (such as polynomial) regression techniques may be used to determine the conversion relationship for the extraneous stimulus, second-order polynomial is generally preferred. Linear or non-linear regression techniques include those available in the MINITAB® version 14 or version 16 statistical packages (MINTAB, INC., State College, Pa.), Microsoft Excel, or other statistical analysis packages providing regression techniques. Preferably, polynomial regression is used to determine the extraneous stimulus conversion relationship. For example in MS Excel version 2010, the Linear Trendline Option accessible through the Trendline Layout Chart Tool may be selected to perform linear regression, while the Polynomial Trendline Option may be chosen to perform a non-linear polynomial regression. Other regression techniques may be used to determine the extraneous stimulus conversion relationship. The extraneous stimulus conversion relationship is preferably stored in the measurement device as a portion of the calibration information.

When linear regression is used, the extraneous stimulus conversion relationship will be in the form of $Y=mX+b$, where m is the slope and b is the intercept of the regression line. When non-linear regression is used, as previously shown, the extraneous stimulus conversion relationship will be in a form of $Y=b_2*X^2+b_1*X+b_0$, and the like, where $b_2$, $b_1$ and $b_0$ are the coefficients of the polynomial. In both the linear or polynomial regression equations, Y is the calculated extraneous stimulus responsive output signal, and X is the extraneous stimulus pseudo-reference concentration. When a value of X (the extraneous stimulus pseudo-reference concentration value) is entered into either one of the relationships (linear or polynomial equations), an output value Y, the calculated extraneous stimulus responsive output signal is generated from the extraneous stimulus conversion relationship and may be used to determine an anchor parameter for an extraneous stimulus.

Multi-variant regression was used to determine a compensation relationship including system error compensation provided by a signal-based anchor parameter (and associated cross-terms) for both the analyte (Ch1 and Ch3) and THb (Ch2 and Ch4), SSP parameters, and other parameters of a %-A1c biosensor system as follows:

For Ch1 and Ch2: DAr1=−0.4057+0.5475*C2MV+1.6776*'D-C2'−0.005466*Mt1+1.9914*'D1-3a'+0.6398*'D1-2'−13.096*'D1-4'+17.282*'D2-4'+287.27*'D2-5'+46.85*'D2-20'+3.6985*DR1C2MV+0.18887*'1-2/1a'+46.85*'1-5/1a'+915.1*'1-5/1aDR1'+0.52306*'1-5/3aA1'−2.8339*'1-2MR1'−0.0702*'1-2/1MR1'.

For Ch3 and Ch4: DAr3=0.6284−2.754*MR3−1517.6*'D3-5'+18.475*'D44'+170.24*'D4-5'+60.17*'D4-20'−1.4066*'DR3D3-1'−0.00736*'3-2/1'−1851.9*'3-5/1aDR3'+178.27*'3-5/2DR3'−4.821*'3-4A3'+35.096*'3-5A3'+0.19912*'3-5/3aA3'+116.13*'3-4MR3'+5527*'3-5MR3'+0.54084*'3-2/1aMR3'.

These compensation relationships show the inclusion of the D-C2 term as the signal-based anchor parameter for THb ($R_{THb\_pseudo}$) and the A3 term as the initial A1c concentration determined from Ch3. As shown in Table 5B, below, including the signal-based anchor parameters for both A1c and THb provided a substantial increase in the compensation relationship for Ch1/Ch2 (A1) and for Ch4/Ch4 (A3) to describe the error in relation to the SSP and other parameters alone.

TABLE 5B

Error in Determined Sample Analyte Concentrations

|  | R-Sq(adj) A1 | R-Sq(adj) A3 |
|---|---|---|
| SSP and Other Parameters | 38.7% | 37.6 |
| Analyte and THb Anchor Parameters, SSP and Other Parameters | 52.1% | 50.6% |

Example 4: Compensation Relationship Including Concentration-Based Anchor Parameters and Other Parameters In this example, the same analysis data and anchor parameters used in Example 2 were used. However, the multi-variant regression also included SSP and other parameters. The pseudo-reference was determined by averaging an initial analyte concentration for each channel.

In this example, system error can be generally expressed for each channel by writing system error (dA/A1cRef or dA3/A1cRef) as a function of a concentration anchor parameter combined with SSP and other parameters as follows: DAr1=dA1/A1cRef=f(DA1=anchor parameter (dA1/A1cAvg), SSP parameters, and other error parameters for Ch1); DAr3=dA3/A1cRef=f(DA3=anchor parameter (dA3/A1cAvg), SSP parameters, and other error parameters for Ch3). These expressions were determined in the laboratory for multiple samples having known reference sample analyte concentrations as determined with a Tosoh G7 reference instrument.

An example of this method to provide a compensation relationship based on concentration-based anchor parameters in combination with SSP and other parameters is as follows. Table 6A and Table 6B show the multi-variant regression results obtained from the SSP and other parameters for Ch1 and Ch3 without the anchor parameter. Table 6C and Table 6D show the multi-variable regression results obtained by including the anchor parameter and its cross-terms with the SSP and other parameters for Ch1 and Ch3. The values on the "Constant" row of the regression output are not weighing coefficients, but a constant for the multi-variant regression equation.

TABLE 6A

Ch1 Multi-variant Regression Results from SSP and Other Parameters.
Ch1 Regression Analysis: DAr1 versus C2MV, MR1, . . .
No anchor parameter, SSP and other parameters only
727 analyses

| Predictor | Coef | SE Coef | T | P |
|---|---|---|---|---|
| Constant | −0.34934 | 0.04948 | −7.06 | 0.000 |
| MR1 | 1.4372 | 0.2200 | 6.53 | 0.000 |
| D1-2 | −0.08388 | 0.04900 | −1.71 | 0.087 |
| 1-5/3aMt1 | −0.16535 | 0.06142 | −2.69 | 0.007 |
| 1-2A1 | −0.012355 | 0.005023 | −2.46 | 0.014 |
| 1-4/3aA1 | −0.08515 | 0.01186 | −7.18 | 0.000 |
| 1-5/3aA1 | 0.52081 | 0.08224 | 6.33 | 0.000 |

S = 0.0504417
R-Sq = 23.8%
R-Sq(adj) = 23.2%

TABLE 6B

Ch3 Multi-variant Regression Results from SSP and Other Parameters.
Ch3 Regression Analysis: DAr3 versus C4MV, D3-2a, . . .
No anchor parameter, SSP and other parameters
727 analyses

| Predictor | Coef | SE Coef | T | P |
|---|---|---|---|---|
| Constant | −0.3799 | 0.1284 | −2.96 | 0.003 |
| C4MV | 0.4449 | 0.1694 | 2.63 | 0.009 |
| D3-2a | 0.6946 | 0.1738 | 4.00 | 0.000 |
| D3-3 | −2.986 | 1.004 | −2.97 | 0.003 |
| D3-5 | 295.91 | 57.83 | 5.12 | 0.000 |
| D3-3/1 | 0.05198 | 0.01432 | 3.63 | 0.000 |
| D3-3/2a | 0.0005234 | 0.0002668 | 1.96 | 0.050 |
| D3-4/2 | −1.1959 | 0.6245 | −1.91 | 0.056 |
| D3-4/3 | −5.344 | 1.189 | −4.49 | 0.000 |
| MR3*D3-2/1a | 0.8573 | 0.1320 | 6.49 | 0.000 |
| MR3*D3-4/3 | 22.757 | 5.512 | 4.13 | 0.000 |
| MR3*D3-5/3 | −18.915 | 7.914 | −2.39 | 0.017 |
| Mt3*D3-2/1a | −0.003637 | 0.001012 | −3.59 | 0.000 |
| Mt3*D3-4/2a | −0.0017349 | 0.0008277 | −2.10 | 0.036 |

S = 0.0532793
R-Sq = 20.4%
R-Sq(adj) = 18.9%

TABLE 6C

Ch1 Multi-variant Regression from Anchor, SSP, and Other Parameters.
Ch1 Regression Analysis: DAr1 versus C2MV, D1-5, . . .
Anchor parameter DA1 and associate cross terms
with SSP and other parameters

| Predictor | Coef | SE Coef | T | P |
|---|---|---|---|---|
| Constant | −0.3422 | 0.1034 | −3.31 | 0.001 |
| C2MV | 0.3060 | 0.1398 | 2.19 | 0.029 |
| D1-5 | 159.82 | 21.50 | 7.43 | 0.000 |
| DA1*C2MV | 1.7524 | 0.8266 | 2.12 | 0.034 |
| DA1*D1-3a | 70.04 | 18.04 | 3.88 | 0.000 |
| DA1*D1-3 | −53.73 | 14.30 | −3.76 | 0.000 |
| D1-2/1 | −0.020109 | 0.004088 | −4.92 | 0.000 |
| DA1*D1-4/1a | 255.82 | 46.75 | 5.47 | 0.000 |
| DA1*D1-4/3 | 15.856 | 3.538 | 4.48 | 0.000 |
| DA1*D1-5/3 | −156.14 | 31.87 | −4.90 | 0.000 |
| DA1*D1-5/3a | 98.25 | 25.06 | 3.92 | 0.000 |
| MR1*D1-2/1a | 0.54276 | 0.07503 | 7.23 | 0.000 |
| Mt1*D1-4/3a | −0.017550 | 0.006175 | −2.84 | 0.005 |

S = 0.0438916
R-Sq = 42.8%
R-Sq(adj) = 41.8%

TABLE 6D

Ch3 Multi-variant Regression from Anchor, SSP, and Other Parameters.
Ch3 Regression Analysis: DAr3 versus DA3, MR3, . . .
Anchor parameter DA3 and associate cross terms
with SSP and other parameters

| Predictor | Coef | SE Coef | T | P |
|---|---|---|---|---|
| Constant | −0.28165 | 0.04108 | −6.86 | 0.000 |
| DA3 | 5.151 | 2.469 | 2.09 | 0.037 |
| MR3 | 0.9509 | 0.1917 | 4.96 | 0.000 |
| D3-2 | −0.08559 | 0.01792 | −4.78 | 0.000 |
| D3-5 | 135.87 | 21.10 | 6.44 | 0.000 |
| DA3*C4MV | −5.699 | 3.401 | −1.68 | 0.094 |
| D3-4/1a | 4.513 | 1.453 | 3.11 | 0.002 |
| D3-4/2a | 0.11812 | 0.05092 | 2.32 | 0.021 |
| D3-4/2 | −1.4066 | 0.6425 | −2.19 | 0.029 |
| DA3*D3-4/1 | −9.629 | 5.368 | −1.79 | 0.073 |
| MR3*D3-4/2a | −0.5884 | 0.2514 | −2.34 | 0.020 |
| Mt3*D3-3/1a | −0.0020053 | 0.0009756 | −2.06 | 0.040 |

TABLE 6D-continued

Ch3 Multi-variant Regression from Anchor, SSP, and Other Parameters.
Ch3 Regression Analysis: DAr3 versus DA3, MR3, . . .
Anchor parameter DA3 and associate cross terms
with SSP and other parameters

| Predictor | Coef | SE Coef | T | P |
|---|---|---|---|---|
| Mt3*D3-3/2 | 0.009898 | 0.004138 | 2.39 | 0.017 |
| S = 0.0436156 | | | | |
| R-Sq = 46.6% | | | | |
| R-Sq(adj) = 45.7% | | | | |

A seen from the example, a substantial improvement in measurement performance of the %-A1c analysis biosensor system was observed when the system error was described by the anchor parameter and its cross-terms in the compensation relationship. For Ch1 (DAr1), the SSP and other parameters provided a $R^2$ (adj) of 23.8%, while when the anchor parameter and cross-terms were added a $R^2$ (adj) of 41.8% was provided. This may be thought of as an approximately 75% (41.8-23.8/23.8*100) increase in the ability of the compensation relationship including the anchor parameter and its associated cross-terms to describe and thus remove error from the Ch1 analysis. The improvement was greater still for Ch3. Thus, the measurement performance of a biosensor system including a compensation relationship addressing system error with an anchor parameter and associated cross-terms would be significantly improved.

Glucose Analyses of Blood

Unlike in the previously described %-Ac analysis biosensor system having two channels and thus two independent analyses performed for the same test sample, in the described glucose analysis system a single analyses was performed using a single working and counter electrode. While a glucose biosensor system could be used that performs two independent analyses, this example shows the diverse applicability to biosensor systems of the compensation relationship including an anchor parameter to compensated for system error.

System error was determined in this example by subtracting the reference analyte concentration of a sample from the analyte concentration of the sample determined from the output signals measured by the measurement device from the sample and a conventional reference correlation and then dividing by the reference analyte concentration. This may be generally expressed as $dG/G_{Ref} = (G_{calc} - G_{Ref})/G_{Ref}$. Glucose was the analyte and the sample was blood. This analysis was performed in the laboratory for multiple samples having known reference sample analyte concentrations as determined with a YSI reference instrument.

The pseudo-reference concentration was determined either by using the analyte sample concentration determined from normalized calibration information, thus normalized output signals and a normalized reference correlation, or through primary compensation that compensated for temperature and the hematocrit effect. As temperature and the hematocrit effect are the most important extraneous stimuli in a glucose analysis, their effect on the determined analyte concentration was substantially reduced either through normalized calibration information (which addresses temperature and may address Hct) or through primary compensation. In this way a pseudo-reference concentration was determined that on average would more accurately describe the reference sample analyte concentration than if the initial analyte concentration were determined from the measured output signals and a conventional reference correlation.

The anchor parameter was determined by subtracting the pseudo-reference concentration from the initial analyte concentration (measured primary output signals/conventional reference correlation) and dividing by the pseudo-reference concentration. This may be generally expressed as $dG/G_{pseudo} = (G_{calc} - G_{pseudo})/G_{pseudo}$.

Unlike the previously described %-A1c analysis biosensor systems, as only one analysis of the blood sample is performed by the glucose biosensor system, if the anchor parameter were used alone for residual compensation, little to no improvement would be observed in relation to the determined pseudo-reference analyte concentration. Thus, in this example the anchor parameter is used in combination with other parameters to determine the compensation relationship using multi-variant regression.

Figure 25:
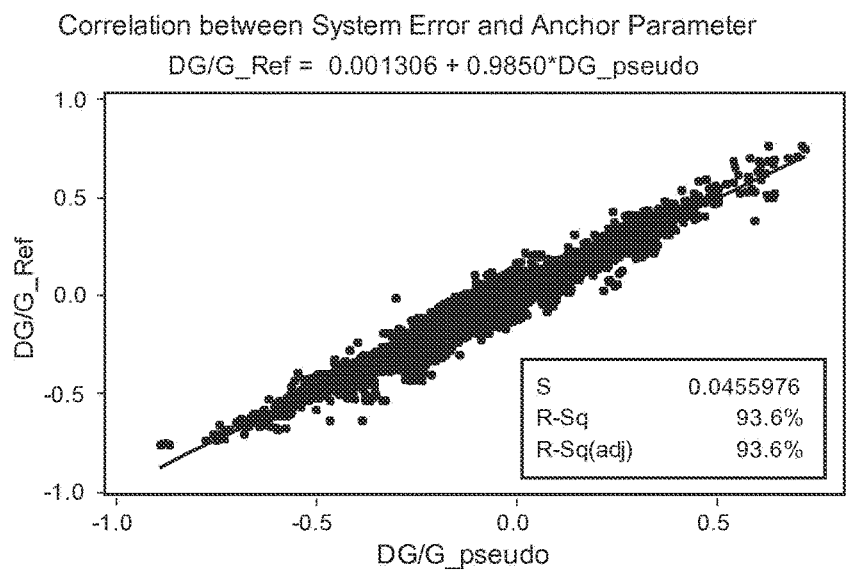
FIG. 25 plots system error against determined anchor parameters.
Figure 26:
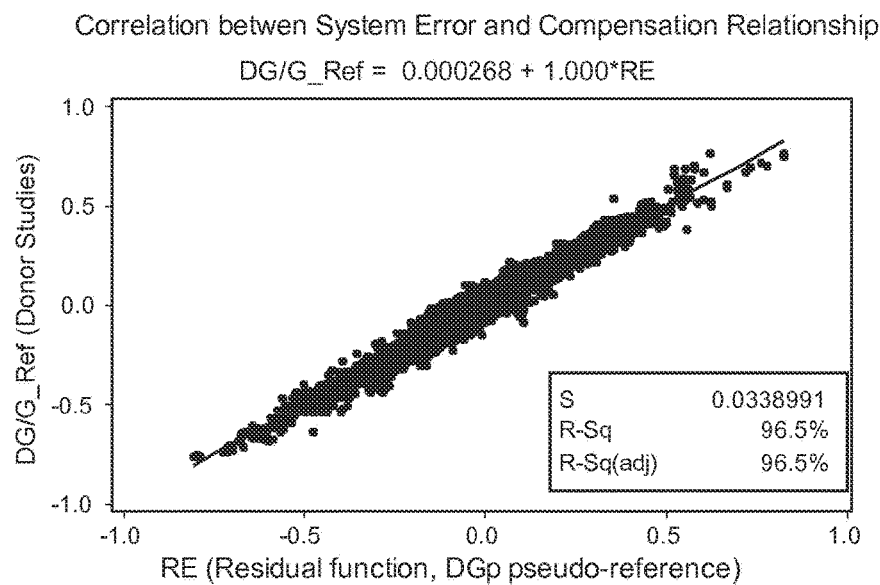
FIG. 26 plots system error against a determined compensation relationship including the anchor parameter and other error parameters.

FIG. 25 plots system error against determined anchor parameters and shows the excellent correlation, in fact, providing an $R^2$ correlation of 93.6% for the samples tested. Thus, the anchor parameter's ability to describe the system error was established. FIG. 26 plots system error against the determined compensation relationship including the anchor parameter and other error parameters, which shows the increased ability of the compensation relationship to describe the system error, providing an $R^2$ correlation of 96.5%. At the same time, the standard deviation of the regression is reduced from 0.0456 to 0.0339, indicating the improvement. Thus, the ability of the compensation relationship including the anchor parameter to compensate for system error during an analysis and thus improve the measurement performance of the biosensor system was established.

Multi-variant regression was used to determine a compensation relationship including system error compensation provided by an anchor parameter (and associated cross-terms) for the single "channel" of a glucose biosensor system as follows:

RE=2.01433−0.0147937*T−1.71565*R65−
0.0046627*R32G+0.0057921*R53G+0.0068783*TR32−
7.571e-5*HR32+1.76e-6*H32G−2.25e-6*H53G+
3.2314*DGp+0.05267*DGT−3.6103e-4*DGH+
0.34475*DGR32−2.2785*DGR65−0.028903*DGR32T−
0.0038475*DG32G+0.016891*DG54G+
0.0128893*DG53G−0.026573*DG64G where T=temperature; R32=R3/2, the ratio of the ending currents of pulse 3 and pulse 2 ($i_{3,4}/i_{2,2}$) as represented in FIG. 5; R43=R4/3, the ratio of the ending currents of pulse 4 and pulse 3 ($i_{4,4}/i_{3,4}$); R54=R5/4, the ratio of the ending currents of pulse 5 and pulse 4 ($i_{5,4}/i_{4,4}$); R53=R5/3, the ratio of the ending currents of pulse 5 and pulse 3 ($i_{5,4}/i_{3,4}$); R65=R6/5, the ratio of the ending currents of pulse 6 and pulse 5 ($i_{6,4}/i_{5,4}$); R64=R6/4, the ratio of the ending currents of pulse 6 and pulse 4 ($i_{6,4}/i_{4,4}$); H32G=$i_{7,4}$ (Hct electrode current)*R32*$G_{initial}$; H53G=$i_{7,4}$*R53*$G_{calc}$; DGp=anchor parameter ($dG/G_{pseudo}$); DGT=DGp*T; DGH=DGp*$i_{7,4}$; and DGR32=DGp*R32.

The regression output from the multi-variant regression, as performed with MINITAB version 16 software using the Multi-Variant Regression of Linear Combinations of Multiple Variables option is as follows in Table 7. The constant for the multi-variant equation was determined as 2.01433.

TABLE 7

Multi-Variant Regression Output including Anchor Parameter

| Predictor | Weighing Coefficient | SE Coef | t | p |
|---|---|---|---|---|
| T | −0.0147937 | 0.0009313 | −15.89 | 0.000 |
| R65 | −1.71565 | 0.04586 | −37.41 | 0.000 |
| R32G | −0.0046627 | 0.0003215 | −14.50 | 0.000 |
| R53G | 0.0057921 | 0.0003846 | 15.06 | 0.000 |
| TR32 | 0.0068783 | 0.0003240 | 21.23 | 0.000 |
| HR32 | −0.00007571 | 0.00000367 | −20.61 | 0.000 |
| H32G | 0.00000176 | 0.00000017 | 10.57 | 0.000 |
| H53G | −0.00000225 | 0.00000020 | −11.26 | 0.000 |
| DGp | 3.2314 | 0.1286 | 25.13 | 0.000 |
| DGT | 0.052670 | 0.002213 | 23.80 | 0.000 |
| DGH | −0.00036103 | 0.00001367 | −26.41 | 0.000 |
| DGR32 | 0.34475 | 0.02110 | 16.34 | 0.000 |
| DGR65 | −2.2785 | 0.1036 | −21.98 | 0.000 |
| DGR32T | −0.028903 | 0.001224 | −23.61 | 0.000 |
| DG32G | −0.0038475 | 0.0002197 | −17.51 | 0.000 |
| DG54G | 0.0168910 | 0.0009121 | 18.52 | 0.000 |
| DG53G | 0.0128893 | 0.0006038 | 21.35 | 0.000 |
| DG64G | −0.026573 | 0.001217 | −21.83 | 0.000 |

S = 0.0339305
R-Sq = 96.5%
R-Sq(adj) = 96.5%

Figure 27:
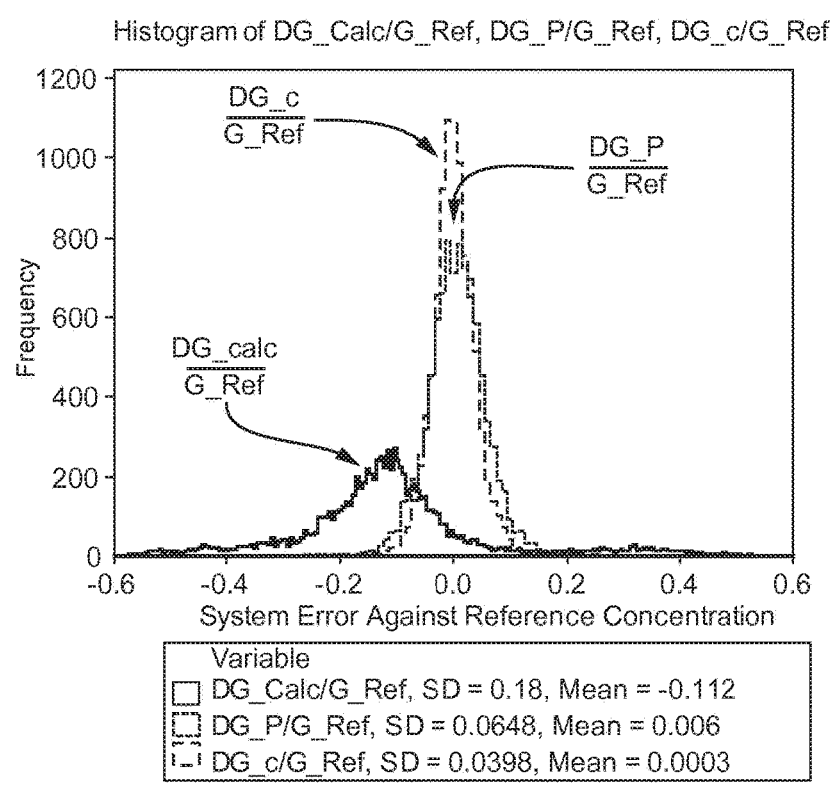
FIG. 27 compares the system error of the initial analyte concentration determined from the measured output signals/conventional reference correlation before any compensation, after compensation with a primary compensation function compensating for temperature and the hematocrit effect but lacking an anchor parameter describing system error, and after compensation by the above-determined compensation relationship including the anchor parameter and the associated cross-terms.

FIG. 27 compares the system error of the initial analyte concentration determined from the measured output signals/conventional reference correlation before any compensation, after compensation with a primary compensation function compensating for temperature and the hematocrit effect but lacking an anchor parameter describing system error, and after compensation by the above-determined compensation relationship including the anchor parameter and the associated cross-terms. The measurement performance increase provided by the compensation relationship including the anchor parameter is most evident in the SD values for each analysis. The SD between the different analyses performed with the compensation relationship including the anchor parameter (SD=0.0398) is approximately 38% (0.0648−0.0398/0.0648*100) below that of the primary compensation alone (SD=0.0648) and approximately 78% (0.18−0.0398/0.18*100) below that of the measured/conventional reference correlation determined analyte concentrations (0.18). Thus, a substantial improvement in accuracy and measurement performance is provided through a compensation relationship including an anchor parameter describing system error for a biosensor error.

FIG. 28 depicts a schematic representation of a biosensor system 500 that determines an analyte concentration in a sample of a biological fluid. Biosensor system 500 includes a measurement device 502 and a test sensor 504. The measurement device 502 may be implemented in an analytical instrument, including a bench-top device, a portable or hand-held device, or the like. Preferably the measurement device 502 is implemented in a hand-held device. The measurement device 502 and the test sensor 504 may be adapted to implement an electrochemical sensor system, an optical sensor system, a combination thereof, or the like.

The biosensor system 500 determines the analyte concentration of the sample using conventional calibration information or the calibration information developed in accord with the previously described normalization techniques and anchor parameter compensation information stored in the measurement device 502. The calibration information from one or both of the calibration methods 100 and 102 may be stored in the measurement device 502. The analysis method 400 may be stored in the measurement device for implementation by the biosensor system 500.

When compensation is implemented by the biosensor system 500, the anchor parameter compensation information may improve the measurement performance of the biosensor system 500 in determining the analyte concentration of the sample. The biosensor system 500 may be utilized to determine analyte concentrations, including those of glucose, A1c, uric acid, lactate, cholesterol, bilirubin, and the like. While a particular configuration is shown, the biosensor system 500 may have other configurations, including those with additional components.

The test sensor 504 has a base 506 that forms a reservoir 508 and a channel 510 with an opening 512. The reservoir 508 and the channel 510 may be covered by a lid with a vent. The reservoir 508 defines a partially-enclosed volume. The reservoir 508 may contain a composition that assists in retaining a liquid sample such as water-swellable polymers or porous polymer matrices. Reagents may be deposited in the reservoir 508 and/or the channel 510. The reagents may include one or more enzymes, binders, mediators, and like species. The reagents may include a chemical indicator for an optical system. The test sensor 504 has a sample interface 514 adjacent to the reservoir 508. The test sensor 504 may have other configurations.

In an optical sensor system, the sample interface 514 has an optical portal or aperture for viewing the sample. The optical portal may be covered by an essentially transparent material. The sample interface 514 may have optical portals on opposite sides of the reservoir 508.

In an electrochemical system, the sample interface 514 has conductors connected to a working electrode 532 and a counter electrode 534 from which the analytic output signal may be measured. The sample interface 514 also may include conductors connected to one or more additional electrodes 536 from which secondary output signals may be measured. The electrodes may be substantially in the same plane or in more than one plane. The electrodes may be disposed on a surface of the base 506 that forms the reservoir 508. The electrodes may extend or project into the reservoir 508. A dielectric layer may partially cover the conductors and/or the electrodes. The sample interface 514 may have other electrodes and conductors.

The measurement device 502 includes electrical circuitry 516 connected to a sensor interface 518 and an optional display 520. The electrical circuitry 516 includes a processor 522 connected to a signal generator 524, an optional temperature sensor 526, and a storage medium 528.

The signal generator 524 is capable of providing an electrical input signal to the sensor interface 518 in response to the processor 522. In optical systems, the electrical input signal may be used to operate or control the detector and light source in the sensor interface 518. In electrochemical systems, the electrical input signal may be transmitted by the sensor interface 518 to the sample interface 514 to apply the electrical input signal to the sample of the biological fluid. The electrical input signal may be a potential or current and may be constant, variable, or a combination thereof, such as when an AC signal is applied with a DC signal offset. The electrical input signal may be applied continuously or as multiple excitations, sequences, or cycles. The signal generator 524 also may be capable of recording an output signal from the sensor interface as a generator-recorder.

The optional temperature sensor 526 is capable of determining the ambient temperature of the measurement device 502. The temperature of the sample may be estimated from the ambient temperature of the measurement device 502, calculated from the output signal, or presumed to be the same or similar to the ambient temperature of the measurement device 502. The temperature may be measured using a thermister, thermometer, or other temperature sensing device. Other techniques may be used to determine the sample temperature.

The storage medium 528 may be a magnetic, optical, or semiconductor memory, another storage device, or the like. The storage medium 528 may be a fixed memory device, a removable memory device, such as a memory card, remotely accessed, or the like.

The processor 522 is capable of implementing the analyte analysis method using computer readable software code and the calibration information and anchor parameter compensation information stored in the storage medium 528. The processor 522 may start the analyte analysis in response to the presence of the test sensor 504 at the sensor interface 518, the application of a sample to the test sensor 504, in response to user input, or the like. The processor 522 is capable of directing the signal generator 524 to provide the electrical input signal to the sensor interface 518. The processor 522 is capable of receiving the sample temperature from the temperature sensor 526. The processor 522 is capable of receiving the output signals from the sensor interface 518.

In electrochemical systems, the analyte responsive primary output signal is generated from the working and counter electrodes 532, 534 in response to the reaction of the analyte in the sample. Secondary output signals also may be generated from additional electrodes 536. In optical systems, the detector or detectors of the sensor interface 518 receive the primary and any secondary output signals. The output signals may be generated using an optical system, an electrochemical system, or the like. The processor 522 is capable of determining analyte concentrations from output signals using the calibration information and the anchor parameter compensation information stored in the storage medium 528. The results of the analyte analysis may be output to the display 520, a remote receiver (not shown), and/or may be stored in the storage medium 528.

The calibration information relating reference sample analyte concentrations and output signals from the measurement device 502 and the anchor parameter compensation information may be represented graphically, mathematically, a combination thereof, or the like. The calibration information and anchor parameter compensation information are preferably represented as correlation equations, which may be represented by a program number (PNA) table, another look-up table, or the like that is stored in the storage medium 528.

Instructions regarding implementation of the analyte analysis including calibration and anchor parameter compensation also may be provided by the computer readable software code stored in the storage medium 528. The code may be object code or any other code describing or controlling the described functionality. The data from the analyte analysis may be subjected to one or more data treatments, including the determination of decay rates, K constants, ratios, functions, and the like in the processor 522.

In electrochemical systems, the sensor interface 518 has contacts that connect or electrically communicate with the conductors in the sample interface 514 of the test sensor 504. The sensor interface 518 is capable of transmitting the electrical input signal from the signal generator 524 through the contacts to the connectors in the sample interface 514. The sensor interface 518 also is capable of transmitting the output signal from the sample through the contacts to the processor 522 and/or signal generator 524.

In light-absorption and light-generated optical systems, the sensor interface 518 includes a detector that collects and measures light. The detector receives light from the test sensor 504 through the optical portal in the sample interface 514. In a light-absorption optical system, the sensor interface 518 also includes a light source such as a laser, a light emitting diode, or the like. The incident beam may have a wavelength selected for absorption by the reaction product. The sensor interface 518 directs an incident beam from the light source through the optical portal in the sample interface 514. The detector may be positioned at an angle such as 45° to the optical portal to receive the light reflected back from the sample. The detector may be positioned adjacent to an optical portal on the other side of the sample from the light source to receive light transmitted through the sample. The detector may be positioned in another location to receive reflected and/or transmitted light.

The optional display 520 may be analog or digital. The display 520 may include a LCD, a LED, an OLED, a vacuum fluorescent display (VFD), or other display adapted to show a numerical reading. Other display technologies may be used. The display 520 electrically communicates with the processor 522. The display 520 may be separate from the measurement device 502, such as when in wireless communication with the processor 522. Alternatively, the display 520 may be removed from the measurement device 502, such as when the measurement device 502 electrically communicates with a remote computing device, medication dosing pump, and the like.

In use, a liquid sample for analysis is transferred into the reservoir 508 by introducing the liquid to the opening 512. The liquid sample flows through the channel 510, filling the reservoir 508 while expelling the previously contained air. The liquid sample chemically reacts with the reagents deposited in the channel 510 and/or reservoir 508.

The test sensor 502 is disposed in relation to the measurement device 502, such that the sample interface 514 is in electrical and/or optical communication with the sensor interface 518. Electrical communication includes the transfer of input and/or output signals between contacts in the sensor interface 518 and conductors in the sample interface 514. Optical communication includes the transfer of light between an optical portal in the sample interface 514 and a detector in the sensor interface 518. Optical communication also includes the transfer of light between an optical portal in the sample interface 514 and a light source in the sensor interface 518.

The processor 522 is capable of directing the signal generator 524 to provide an input signal to the sensor interface 518 of the test sensor 504. In an optical system, the sensor interface 518 is capable of operating the detector and light source in response to the input signal. In an electrochemical system, the sensor interface 518 is capable of providing the input signal to the sample through the sample interface 514. The test sensor 504 is capable of generating one or more output signals in response to the input signal. The processor 522 is capable of receiving the output signals generated in response to the redox reaction of the analyte in the sample as previously discussed.

The processor 522 is capable of transforming the output signal using the analysis method and the calibration information stored in the storage medium 528 to determine an initial analyte concentration of the sample. The processor 522 may then report this initial analyte concentration. The processor 522 is capable of implementing anchor parameter compensation to determine the final analyte concentration of the sample. More than one compensation and/or other function also may be implemented by the processor 522.

To provide a clear and more consistent understanding of the specification and claims of this application, the following definitions are provided.

"Average" or "Averaged" or "Averaging" includes the combination of two or more variables to form an average variable. A variable may be a numerical value, an algebraic or scientific expression, or the like. For example, averaging may be performed by adding the variables and dividing the sum by the number of variables; such as in the equation AVG=(a+b+c)/3, where AVG is the average variable and a, b, and c are the variables. In another example, averaging includes modifying each variable by an averaging coefficient and then adding the modified variables to form a weighted average; such as in the equation $W_{AVG}=0.2*a+0.4*b+0.4*c$, where $W_{AVG}$ is the weighted average, 0.2, 0.4 and 0.4 are the averaging coefficients, and a, b, and c are the variables. The averaging coefficients are numbers between 0 and 1; and if added, will provide a sum of 1 or substantially 1. Other averaging methods may be used.

"Weighing Coefficients" apportion the contribution of each term to the relationship. Weighing coefficients are numbers between 0 and 1, but excluding 0 and 1, and if added, will provide a sum of 1 or substantially 1. A weighing coefficient cannot be 1 as it does not apportion the contribution of the term to the relationship, and a weighing coefficient cannot be 0, as it results in the exclusion of the term from the relationship. Thus, weighing coefficients allow for each term to have a different apportionment to the relationship. Two or more of the term weighing coefficients may be the same or similarly apportion the contribution of their respective terms to the function. However, at least two weighing coefficients are different or differently apportion the contribution of their respective terms to the relationship. In this way, the term weighing coefficients may be selected to allow for the effect of one term on another term in relation to the overall function, thus reducing or eliminating error from the interactions of the terms when a complex index function is used. The term weighing coefficients are not a single value or constant that may be applied by algebraic disposition to all the terms. The weighing coefficients for terms may be determined through a mathematical technique, such as the statistical processing of the data collected from a combination of multiple analyte concentrations, different hematocrit levels, different total hemoglobin levels, different temperatures, and the like. Weighing coefficients for the terms may be determined through other mathematical techniques including different statistical processing methods. Preferably, multi-variant regression techniques including one or more exclusion tests are used to determine weighing coefficients for the terms.

A "complex index function" is an index function having terms modified by weighing coefficients. A complex index function preferably is not "complex" in a mathematical sense, thus does not require or imply the use of an imaginary number (a number with the square root of negative one). However, a complex index function may include one or more imaginary numbers, but is not limited or restricted to having any imaginary numbers.

"Measurable species" addresses a species the biosensor system is designed to determine the presence and/or concentration of in the sample and may be the analyte of interest or a mediator whose concentration in the sample is responsive to that of the analyte of interest.

While various embodiments of the invention have been described, it will be apparent to those of ordinary skill in the art that other embodiments and implementations are possible within the scope of the invention.

What is claimed is:

1. A method of operating a biosensor system for determining an analyte concentration in a sample, the method comprising:
providing a biosensor system in the form of an analytical instrument including
a measurement device having electrical circuitry communicatively coupled to a processor, a storage medium, a signal generator, and a sensor interface, the processor having instructions and data stored in the storage medium, and
a test sensor having a base and a sample interface, the base forming a reservoir and a channel with an opening, the reservoir being in electrical or optical communication with the measurement device;
receiving a biological fluid sample in the opening of the reservoir, the biological fluid sample flowing through the channel to fill at least in part the reservoir of the test sensor, the biological fluid sample including the analyte;
in response to receiving the biological fluid sample in the reservoir, generating an input signal, by the processor, from the signal generator;
transmitting the input signal by the sensor interface to the sample interface for applying the input signal to the biological fluid sample;
in response to the input signal and a concentration of an analyte in the biological fluid sample, generating and measuring, by the processor, at least one analyte responsive output signal from the test sensor, the at least one analyte responsive output signal being one or more of an electrical output signal generated by a redox reaction or a light-generated output signal in response to a light-identifiable species;
determining, by the processor, a pseudo-reference concentration value from the at least one analyte responsive output signal, the pseudo-reference concentration value being a substitute for true relative error;
determining, by the processor, at least one anchor parameter in response to the pseudo-reference concentration value, the at least one anchor parameter compensating for system error and being determined by subtracting the pseudo-reference concentration value from an initial analyte concentration determined with the measurement device, and then, dividing by the pseudo-reference concentration value;
incorporating, by the processor, the at least one anchor parameter into a compensation relationship;
determining, by the processor, a final compensated analyte concentration of the biological fluid sample in response to the compensation relationship; and
outputting, by the processor, the final compensated analyte concentration to one or more of a display, a remote receiver, or a storage medium.

2. The method of claim 1, further comprising:
measuring at least one extraneous stimulus responsive output signal from the biological fluid sample;
selecting a sample analyte concentration value as the pseudo-reference concentration value, where the sample analyte concentration value for multiple analyses is on average closer to an actual analyte concentration of the biological fluid sample than would be independently determined from the one analyte responsive output signal; and determining the pseudo-reference concentration value in response to the one analyte responsive output signal and primary compensation determining the at least one anchor parameter in response to the pseudo-reference concentration value and one analyte responsive output signal, where the at least one anchor parameter is a concentration anchor parameter= (the initial analyte concentration determined from the one analyte responsive output signal without compensation the pseudo-reference concentration value determined with compensation)/the pseudo-reference concentration value determined with compensation.

3. The method of claim 1,
where the measuring at least one analyte responsive output signal comprises measuring at least two analyte responsive output signals from the biological fluid sample and
where the determining a pseudo-reference concentration value comprises selecting a sample analyte concentration value as the pseudo-reference concentration value, where the sample analyte concentration value for multiple analyses is on average closer to an actual analyte concentration of the biological fluid sample than would be independently determined from the at least two analyte responsive output signals.

4. The method of claim 3, where the determining a pseudo-reference concentration value comprises:
determining the initial analyte concentration of each of the at least two analyte responsive output signals and averaging the initial analyte concentrations.

5. The method of claim 3, where the determining at least one anchor parameter comprises:
determining a first anchor parameter in response to a first normalized output signal value and a pseudo-reference signal, where the first normalized output signal value is responsive to a first analyte response output signal and a normalizing relationship;
determining a second anchor parameter in response to a second normalized output signal value and the pseudo-reference signal, where the second normalized output signal value is responsive to a second analyte response output signal and the normalizing; and
determining the pseudo-reference signal in response to the pseudo-reference concentration value and a normalized reference correlation.

6. The method of claim 5,
where the first anchor parameter comprises a first signal anchor parameter=$(NR_{OSV1}-NR_{Pseudo})/NR_{Pseudo}$, where $NR_{OSV1}$ is the first normalized output signal value and $NR_{Pseudo}$ is the pseudo-reference signal and
where the second anchor parameter comprises a second signal anchor parameter=$(NR_{OSV2}-NR_{Pseudo})/NR_{Pseudo}$, where $NR_{OSV2}$ is the second normalized output signal value and $NR_{Pseudo}$ is the pseudo-reference signal value.

7. The method of claim 5, further comprising:
determining the normalizing relationship between at least two analyte responsive output signals and at least two quantified extraneous stimulus values;
determining the at least two quantified extraneous stimulus values from the at least one extraneous stimulus responsive output signal;

measuring at least one extraneous stimulus responsive output signal from at least one reference biological fluid sample;
determining a reference correlation between a reference sample analyte concentration of the at least one reference biological fluid sample and at least two analyte responsive output signals;
determining the at least one normalized reference correlation between at least two normalized analyte responsive output signals and the reference sample analyte concentration; and
determining the at least two normalized analyte responsive output signals from the at least two analyte responsive output signals and the normalizing value.

8. The method of claim 7, where determining the normalizing relationship comprises applying a normalizing relationship regression technique to the at least two analyte responsive output signals and the at least two quantified extraneous stimulus values at a single selected analyte concentration, and where determining the at least one normalized reference correlation comprises applying a normalized reference correlation regression technique to the at least two normalized analyte responsive output signals and the at least one reference sample analyte concentration.

9. The method of claim 7, further comprising:
determining at least two second quantified extraneous stimulus values from the at least one extraneous stimulus responsive output signal;
determining a second normalizing relationship between the at least two normalized analyte responsive output signals and the at least two second quantified extraneous stimulus values;
determining at least two second normalized analyte responsive output signals from the at least two normalized analyte responsive output signals and a second normalizing value; and
determining a second normalized reference correlation between the at least two second normalized analyte responsive output signals and the at least one reference sample analyte concentration.

10. The method of claim 9, where the determining a second normalizing relationship comprises applying a second normalizing relationship regression technique to the at least two normalized analyte responsive output signals and the at least two second quantified extraneous stimulus values at a single selected analyte concentration, and where determining a second normalized reference correlation comprises applying a second normalized reference correlation regression technique to the at least two second normalized analyte responsive output signals and the at least one reference sample analyte concentration.

11. A biosensor system for determining an analyte concentration in a biological fluid sample, the biosensor system being an optical system or an electrochemical system, the biosensor system comprising:
a test sensor having a base and a sample interface, the base forming a reservoir and a channel with an opening, the opening being configured to receive a biological fluid sample and to allow the biological fluid sample to flow through the channel to fill at least in part the reservoir;
a measurement device in electrical or optical communication with the reservoir, the measurement device having electrical circuitry communicatively coupled to a processor, a storage medium, a signal generator, and a sensor interface, the processor having instructions and data stored in the storage medium, the instructions configured such that when executed by the processor the system is enabled so that:

in response to receiving the biological fluid sample in the reservoir, the signal generator applies an electrical or optical input signal to the sensor interface, the input signal is transmitted by the sensor interface to the sample interface for applying the input signal to the biological fluid sample, in response to the input signal and to the concentration of the analyte in the biological fluid sample, the processor generates and measures at least one analyte responsive output signal, the output signal being one or more of a light-generated output signal in response to a light-identifiable species and an electrical output signal generated by a redox reaction, where the processor is capable of measuring at least one analyte responsive output signal, the processor determines a pseudo-reference concentration value from the at least one analyte responsive output signal, where a pseudo-reference concentration value is a substitute for true relative error, the processor determines at least one anchor parameter in response to the pseudo-reference concentration value, the at least one anchor parameter compensating for system error and being determined by subtracting the pseudo-reference concentration value from an initial analyte concentration determined with the measurement device, and then, dividing by the pseudo-reference concentration value, the processor incorporates the at least one anchor parameter into a compensation relationship, the processor determines a final compensated analyte concentration of the biological fluid sample in response to the compensation relationship, and the processor outputs the final compensated analyte concentration to one or more of a display, a remote receiver, or a storage medium.

12. The biosensor system of claim 11, wherein the system is further enabled so that:

the processor measures at least one extraneous stimulus responsive output signal and the processor determines a pseudo-reference concentration value that comprises selecting a sample analyte concentration value as the pseudo-reference concentration value, the sample analyte concentration value for multiple analyses being on average closer to an actual analyte concentration of the biological fluid sample than would be independently determined from the one analyte responsive output signal.

13. The biosensor system of claim 12, wherein the system is further enabled so that the processor determines the pseudo-reference concentration value in response to the one analyte responsive output signal and primary compensation.

14. The biosensor system of claim 13, wherein the system is further enabled so that the processor determines the at least one anchor parameter in response to the pseudo-reference concentration value and the one analyte responsive output signal.

15. The biosensor system of claim 14, where the at least one anchor parameter is a concentration anchor parameter= (the initial analyte concentration determined from the one analyte responsive output signal without compensation the pseudo-reference concentration value determined with compensation)/the pseudo-reference concentration value determined with compensation.

* * * * *